(12) United States Patent
Carola et al.

(10) Patent No.: US 9,044,409 B2
(45) Date of Patent: Jun. 2, 2015

(54) USE OF CHROMEN-4-ONE DERIVATIVES

(75) Inventors: Christophe Carola, Langen (DE);
Herwig Buchholz, Frankfurt (DE);
Sylvia Huber, Darmstadt (DE); Ralf Rosskopf, Muenster (DE)

(73) Assignee: Merck Patent GmbH, Darmstadt (DE)

( * ) Notice: Subject to any disclaimer, the term of this patent is extended or adjusted under 35 U.S.C. 154(b) by 1610 days.

(21) Appl. No.: 11/869,192

(22) Filed: Oct. 9, 2007

(65) Prior Publication Data
US 2008/0027133 A1 Jan. 31, 2008

Related U.S. Application Data

(63) Continuation of application No. 10/920,202, filed on Aug. 18, 2004, now abandoned.

(30) Foreign Application Priority Data

Aug. 18, 2003 (DE) .................................. 103 37 863

(51) Int. Cl.
| | |
|---|---|
| A61K 31/05 | (2006.01) |
| A61K 31/122 | (2006.01) |
| A61K 31/35 | (2006.01) |
| A61K 31/352 | (2006.01) |
| A61K 8/49 | (2006.01) |
| A23L 1/30 | (2006.01) |
| A61K 45/06 | (2006.01) |
| A61Q 5/00 | (2006.01) |
| A61Q 17/04 | (2006.01) |
| A61Q 19/00 | (2006.01) |
| A61Q 19/08 | (2006.01) |
| A61Q 11/00 | (2006.01) |
| A61Q 19/02 | (2006.01) |

(52) U.S. Cl.
CPC .................. *A61K 8/498* (2013.01); *A61K 31/05* (2013.01); *A61K 31/122* (2013.01); *A23L 1/30* (2013.01); *A61K 31/35* (2013.01); *A61K 31/352* (2013.01); *A61K 45/06* (2013.01); *A61K 2800/782* (2013.01); *A61Q 5/00* (2013.01); *A61Q 11/00* (2013.01); *A61Q 17/04* (2013.01); *A61Q 19/00* (2013.01); *A61Q 19/007* (2013.01); *A61Q 19/02* (2013.01); *A61Q 19/08* (2013.01)

(58) Field of Classification Search
CPC ..... A61K 31/05; A61K 31/122; A61K 31/35; A61K 31/352
USPC .......................................................... 514/456
See application file for complete search history.

(56) References Cited

U.S. PATENT DOCUMENTS

| | | | |
|---|---|---|---|
| 6,001,961 | A | 12/1999 | Jonczyk et al. |
| 6,559,144 | B2 | 5/2003 | Diefenbach et al. |
| 6,743,810 | B2 | 6/2004 | Wiesner et al. |
| 2005/0095305 | A1 | 5/2005 | Arias et al. |

FOREIGN PATENT DOCUMENTS

| | | |
|---|---|---|
| JP | 54032638 A | 3/1979 |
| JP | 58-062112 | 4/1983 |
| JP | 05301813 A | 11/1993 |
| JP | 07-188208 | 7/1995 |
| WO | WO 97/03657 A | 7/1996 |
| WO | WO 98/35949 A | 8/1998 |
| WO | WO-99/47119 | 9/1999 |
| WO | WO-00/03707 | 1/2000 |

(Continued)

OTHER PUBLICATIONS

Kao Corp., "Skin External Preparation," Patent Abstracts of Japan, Publication Date: Jul. 25, 1995, English Abstract of JP 07-188208.
Mitsubishi Electric Corp., "Azimuth Display Device," Patent Abstracts of Japan, Publication Date: Feb. 25, 1983; English Abstract of JP 58-032112.
Bunger, Joachim et al., "Use of ectoin or ectoin derivatives for the prophylaxis and/or treatment of UV-induced immunosuppression," NERAC, Publication Date: Oct. 4, 2001; English Abstract of WO 2001/072287.

(Continued)

*Primary Examiner* — Yong Chong
(74) *Attorney, Agent, or Firm* — Millen, White, Zelano & Branigan, P.C.

(57) ABSTRACT

The invention relates to the use of chromen-4-one derivatives of the formula I

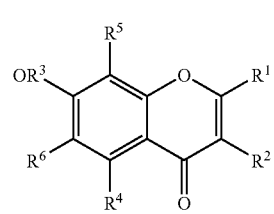

where $R^1$ and $R^2$ may be identical or different and are selected from H, —C(=O)—$R^7$, —C(=O)—O$R^7$, alkyl groups, alkenyl groups, hydroxyalkyl groups and/or cycloalkyl groups and/or cycloalkenyl groups, $R^3$ is H or alkyl groups, $R^4$ is H or O$R^8$, $R^5$ and $R^6$ are selected from —H, —OH, alkyl groups, alkenyl groups and hydroxyalkyl groups, and $R^7$ is H, alkyl groups, a polyhydroxyl compound, such as, preferably, an ascorbic acid radical or glycosidic radicals, and $R^8$ is H or alkyl groups, where at least two of the substituents $R^1$, $R^2$ and $R^4$-$R^6$ are different from H or at least one substituent from $R^1$ and $R^2$ is —C(=O)—$R^7$ or —C(=O)—O$R^7$, for the care, preservation or improvement of the general state of the skin or hair.

10 Claims, No Drawings

(56) References Cited

FOREIGN PATENT DOCUMENTS

| WO | WO 00/26212 | 5/2000 |
| WO | WO 01/28473 A | 10/2000 |
| WO | WO 01/58893 A | 8/2001 |
| WO | WO-01/72287 | 10/2001 |
| WO | WO 02/041910 A | 10/2001 |
| WO | WO-03/043595 | 5/2003 |

OTHER PUBLICATIONS

Arias, Carmen et al., "Anti-Aging Agents," NERAC, Publication Date: May 30, 2003; English Abstract of WO03/043595.

Darro, Francis et al., "Therapeutic composition based on flavonoids for use in the treatment of tumours with cytotoxic agents," NERAC, Publication Date: Jan. 27 2000; English Abstract of WO00/03707.

USE OF CHROMEN-4-ONE DERIVATIVES

This application is a continuation application of U.S. Ser. No. 10/920,202, filed on Aug. 18, 2004 now abandoned.

The present invention relates to the use of chromen-4-one derivatives for the care, preservation or improvement of the general state of the skin or hair and for prophylaxis against time- and/or light-induced ageing processes of the human skin or human hair and for the prophylaxis and/or treatment of skin diseases. The invention furthermore relates to compositions having an effective content of chromen-4-one derivatives. In particular, the present invention relates to cosmetic compositions for prophylaxis against ageing processes in the skin.

The human skin is subject to certain ageing processes, some of which are attributable to intrinsic processes (chronoageing) and some of which are attributable to exogenous factors (environmental, for example photo-ageing). In addition, temporary or even lasting changes to the skin picture can occur, such as acne, greasy or dry skin, keratoses, rosaceae, light-sensitive, inflammatory, erythematous, allergic or autoimmune-reactive reactions, such as dermatosis and photodermatosis.

The exogenous factors include, in particular, sunlight or artificial radiation sources having a comparable spectrum, and compounds which can be formed by the radiation, such as undefined reactive photoproducts, which may also be free-radical or ionic. These factors also include cigarette smoke and the reactive compounds present therein, such as ozone, free radicals, for example the hydroxyl free radical, singlet oxygen and other reactive oxygen or nitrogen compounds which interfere with the natural physiology or morphology of the skin.

The influence of these factors can result, inter alia, in direct damage to the DNA of the skin cells and to the collagen, elastin or glycosaminoglycan molecules of the extracellular matrix, which are responsible for the strength of skin. In addition, the signal transduction chains, which are terminated by the activation of matrix-degrading enzymes, may be affected. Important representatives of these enzymes are the matrix metallo-proteinases (MMPs, for example collagenases, gelatinases and stromelysins), whose activity is additionally regulated by TIMPs (tissue inhibitors of matrix metalloproteinases).

The consequences of the above-mentioned ageing processes are thinning of the skin, weaker interlacing of epidermis and dermis, and a reduction in the number of cells and the supplying blood vessels. This results in the formation of fine lines and wrinkles, the skin becomes leathery, and pigment defects can occur.

The same factors also act on hair, where damage can likewise occur. The hairs become brittle, less elastic and dull. The surface structure of the hairs is damaged.

Cosmetic or dermatological care products having properties which are claimed to counter the processes described or comparable processes or reduce or reverse the harmful consequences thereof are frequently distinguished by the following specific properties—free-radical-scavenging, antioxidative, inflammation-inhibiting or humectant. They prevent or reduce, inter alia, the activity of matrix-degrading enzymes or regulate the new synthesis of collagen, elastin or proteoglycans.

The use of antioxidants or free-radical scavengers in cosmetic compositions is adequately known per se. Thus, the use of the antioxidative vitamin E in sunscreen formulations is usual. Nevertheless, the effect achieved is even here well short of the hoped-for effect.

Vitamin A and vitamin-A derivatives, such as retinoic acid, retinol and retinol esters, act on the differentiation of epithelial cells and are therefore employed for the prophylaxis and treatment of numerous phenomena which impair the skin state, for example use against acne, psoriasis, senile keratosis, skin discoloration and wrinkles has been described (cf., for example, WO 93/19743 and WO 02/02074).

However, a skin-irritant effect of retinol and derivatives is also described in the literature (for example WO 94/07462). These side effects restrict the use of retinol to narrowly limited areas, it being necessary to avoid over-dosing. There is therefore a demand for active ingredients which have a retinol-like spectrum of action, but do not have the side effects described or at least only do so in reduced form.

Owing to the constantly increasing demand for active ingredients for the preventative treatment of human skin and human hair against ageing processes and harmful environmental influences, the object of the present invention was to provide novel active ingredients which exhibit the effects already mentioned at the outset, are sufficiently oxidation- and photostable and can readily be formulated. The compositions prepared therewith should furthermore have as far as possible a low irritation potential for the skin, as far as possible have a positive influence on water binding in the skin, retain or increase skin elasticity and thus promote smoothing of the skin. In addition, they should preferably create a pleasant skin feeling on application to the skin.

Surprisingly, it has now been found that certain chromen-2-one derivatives (chromone derivatives) are suitable as active ingredients having the profile described.

The present invention relates firstly to the use of at least one compound of the formula I

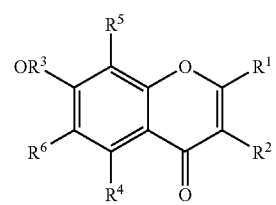

I or of a composition comprising at least one compound of the formula I, where $R^1$ and $R^2$ may be identical or different and are selected from
—H, —C(=O)—$R^7$ and —C(=O)—$OR^7$,
straight-chain or branched $C_1$- to $C_{20}$-alkyl groups,
straight-chain or branched $C_3$- to $C_{20}$-alkenyl groups,
straight-chain or branched $C_1$- to $C_{20}$-hydroxyalkyl groups, where the hydroxyl group may be bonded to a primary or secondary carbon atom of the chain and furthermore the alkyl chain may also be interrupted by oxygen, and/or
$C_3$- to $C_{10}$-cycloalkyl groups and/or $C_3$- to $C_{12}$-cycloalkenyl groups, where the rings may each also be bridged by —(CH$_2$)$_n$— groups, where n=1 to 3,
$R^3$ is H or straight-chain or branched $C_1$- to $C_{20}$-alkyl groups,
$R^4$ is H or $OR^8$,
$R^5$ and $R^6$ may be identical or different and are selected from
—H and —OH,
straight-chain or branched $C_1$- to $C_{20}$-alkyl groups,
straight-chain or branched $C_3$- to $C_{20}$-alkenyl groups,
straight-chain or branched $C_1$- to $C_{20}$-hydroxyalkyl groups, where the hydroxyl group may be bonded to a primary or secondary carbon atom of the chain and furthermore the alkyl chain may also be interrupted by oxygen, and $R^7$ is H, straight-chain or branched $C_1$- to $C_{20}$-alkyl groups, a polyhydroxyl compound, such as, preferably, an ascorbic acid radical or glycosidic radicals, and $R^8$ is H or straight-chain or branched $C_1$- to $C_{20}$-alkyl groups, where at least two of the substituents $R^1$, $R^2$ and $R^4$-$R^6$ are different from H or at least one substituent from $R^1$ and $R^2$ is —C(=O)—$R^7$ or —C(=O)—$OR^7$, for the care, preservation or improvement of the general state of the skin or hair.

For the purposes of the present invention, the term "compound of the formula I" basically also includes the salts of the compounds of the formula I. The preferred salts here include, in particular, alkali metal and alkaline earth metal salts as well as ammonium salts, but in particular sodium and potassium salts.

The present invention furthermore relates to a composition comprising at least one compound of the formula I containing radicals as defined above, and at least one further skin-care ingredient and at least one carrier which is suitable for topical applications.

Uses which are preferred in accordance with the invention of the compounds of the formula I or of compositions comprising at least one compound of the formula I are, in particular, the use for prophylaxis against time- and/or light-induced ageing processes of the human skin or human hair, in particular for prophylaxis against dry skin, wrinkle formation and/or pigment defects, and/or for the reduction or prevention of the harmful effects of UV rays on the skin, and for prophylaxis against or reduction of skin unevenness, such as wrinkles, fine lines, rough skin or large-pored skin.

Uses which are preferred in accordance with the invention of the compounds of the formula I or of compositions comprising at least one compound of the formula I are furthermore the use for the prophylaxis and/or prevention of premature skin ageing, in particular for the prophylaxis and/or prevention of light- or ageing-induced wrinkling of the skin, for the reduction of pigmentation and keratosis actinica, and for the prophylaxis and/or treatment of all diseases which are associated with normal skin ageing or light-induced ageing of the skin, and for the prophylaxis and/or treatment of skin diseases which are associated with defective keratinisation relating to differentiation and cell proliferation, in particular for the treatment of acne vulgaris, acne comedonica, polymorphic acne, acne rosaceae, nodular acne, acne conglobata, age-related acne, acne occurring as a side effect, such as acne solaris, medicament-related acne or acne professionalis, for the treatment of other defects of keratinisation, in particular ichthyosis, ichthyosiform states, Darier's disease, keratosis palmoplantaris, leukoplasia, leukoplasiform states, skin and mucosal (buccal) eczema (lichen), for the treatment of other skin diseases which are associated with defective keratinisation and have an inflammatory and/or immunoallergic component, and in particular all forms of psoriasis relating to the skin, mucous membranes and finger- and toenails, and psoriatic rheumatism and skin atopy, such as eczema, or respiratory atopy, or also hypertrophy of the gums, and for the prophylaxis and/or treatment of all benign or malignant excrescence of the dermis or epidermis, which may be of viral origin, such as verruca vulgaris, verruca plana, epidermodysplasia verruciformis, oral papillomatosis, papillomatosis florida, and excrescence which may be caused by UV radiation, in particular epithelioma baso-cellulare and epithelioma spinocellulare.

The present invention also relates to the use of the compounds of the formula I for the preparation of compositions which are suitable for the above-mentioned uses.

The compositions here are usually either compositions which can be used topically, for example cosmetic or dermatological formulations, or foods or food supplements. In this case, the compositions comprise a cosmetically or dermatologically or food-suitable carrier and, depending on the desired property profile, optionally further suitable constituents.

The use according to the invention of chromen-4-one derivatives of the general formula I in compositions offers, inter alia, protection against damage caused directly or indirectly by UV radiation or by processes caused by reactive compounds, such as, for example, skin ageing, loss of skin moisture, loss of skin elasticity, formation of wrinkles or folds or of pigment defects or senile keratosis.

The present invention furthermore relates to the use of the above-mentioned compositions for the prevention of undesired changes to the skin picture, such as, for example, acne or greasy skin, keratoses, light-sensitive, inflammatory, erythematous, allergic or autoimmune-reactive reactions.

However, the compounds and compositions according to the invention preferably also serve to calm sensitive and irritated skin, for the preventative regulation of collagen, hyaluronic acid and elastin synthesis, stimulation of DNA synthesis, in particular in the case of deficient or hypoactive skin states, regulation of the transcription and translation of matrixdegrading enzymes, in particular of MMPS, increase in cell regeneration and regeneration of the skin, increase in the skin's own protective and repair mechanisms for DNA, lipids and/or proteins.

Preferred compounds of the formula I are characterised in that $R^3$ is H and $R^4$ is OH, since the action potential of representatives of this class of compound is particularly high in the above-mentioned sense. If, in addition, at least one of the radicals $R^5$ and $R^6$ is OH, these preferred compounds, in addition to the above-mentioned properties, additionally have an anti-oxidant potential. They can therefore simultaneously function as anti-oxidant in compositions.

Other preferred compounds of the formula I are characterised in that $R^5$ and $R^6$ are H. In this case, the radicals $R^3$ and $R^4$ are freely accessible, which, as assumed, is advantageous for interaction with enzymes involved in the effects mentioned.

Likewise preferred compounds of the formula I are characterised in that one of the radicals $R^1$ and $R^2$ is H and the other radical is —C(=O)—$R^7$, —C(=O)—$OR^7$ or a straight-chain or branched $C_1$- to $C_{20}$-alkyl group.

In addition, compounds which are preferred in accordance with the invention have advantages on incorporation into the compositions:
mono- and/or oligoglycosyl radicals improve the water solubility of the compounds to be employed in accordance with the invention;
straight-chain or branched $C_1$- to $C_{20}$-alkoxy groups, in particular the long-chain alkoxy functions, such as ethylhexyloxy groups, increase the oil solubility of the compounds;

i.e. the hydrophilicity or lipophilicity of the compounds according to the invention can be increased through a suitable choice of the substituents.

Glycosidic radicals which can be employed are in particular mono- or oligosaccharide radicals. Preference is given here to hexosyl radicals, in particular ramnosyl radicals and glucosyl radicals. However, other hexosyl radicals, for example allosyl, altrosyl, galactosyl, gulosyl, idosyl, mannosyl and talosyl, may also advantageously be used. It may also be advantageous to use pentosyl radicals. The glycosyl radicals may be linked to the basic structure by means of an α- or β-glycosidic link. A preferred disaccharide is, for example, 6-O-(6-deoxy-α-L-mannopyranosyl)-β-D-glucopyranoside.

However, in likewise preferred embodiments of the invention, the compositions according to the invention may also comprise compounds of the formula I which are sparingly soluble or insoluble in the composition matrix. In this case, the compounds are preferably dispersed in finely divided form in the cosmetic composition.

Particular preference is given to the use of compounds selected from the compounds of the formulae Ia-In:

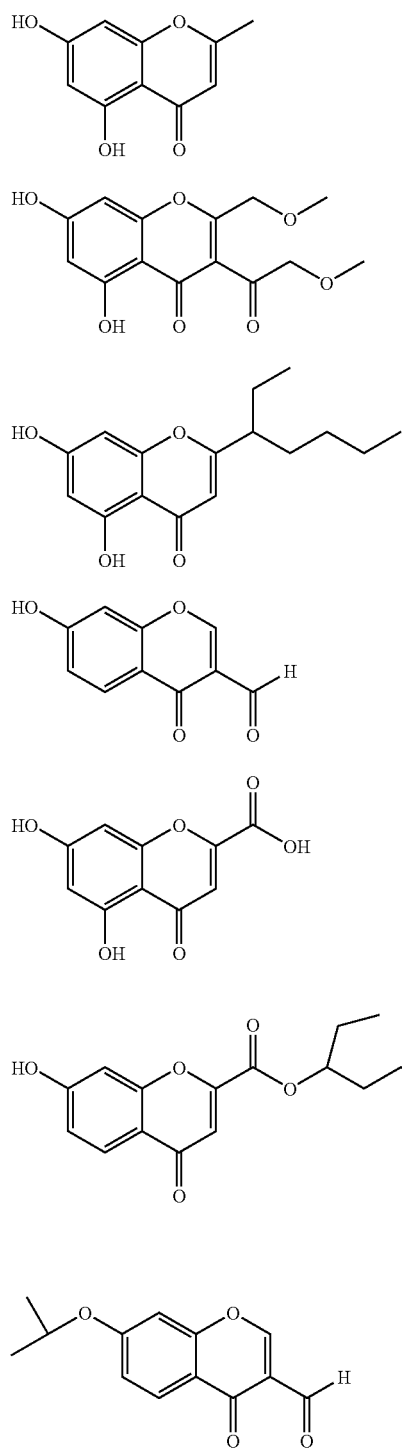

-continued

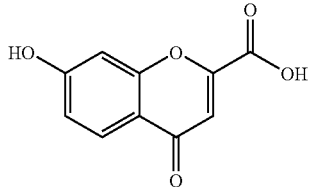

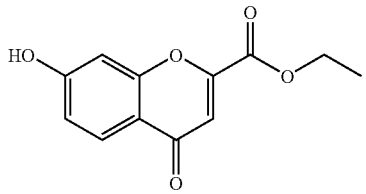

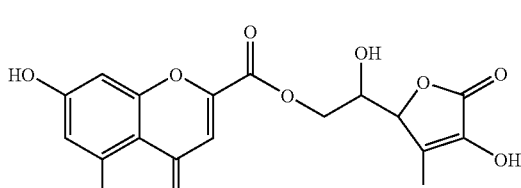

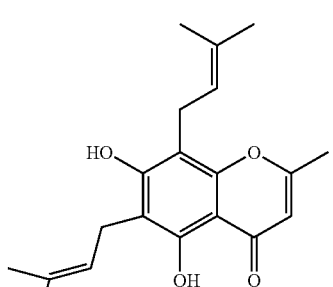

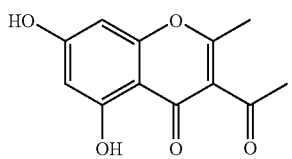

Applications of structurally related compounds are known from the literature:

The use of certain 2-(alkyl)carboxyl- or 2-(alkyl)phenyl-substituted chromen-4-one derivatives in combination with divalent zinc in pharmaceutical and cosmetic compositions is disclosed in EP-A-0 304 802. The compositions are suitable for the treatment of skin, in particular for the treatment of dermatoses, including atopic eczema.

EP-A-0 424 444 discloses the use of salts of chromonecarboxylic acid in cosmetics for combating skin ageing. The compound exhibits a UV-filtering action here and has the following effects in animal experiments: the proportion of bound lipids in the skin increases, the proportion of soluble collagen in the skin is increased, the resistance of the skin to the effects of the fibroplatic proteases coliagenase and elastase is increased.

U.S. Pat. No. 6,019,992 discloses cosmetic compositions which comprise 4-chromanone and are suitable for the treatment of aged, dry or wrinkled skin. It is shown here that 4-chromanone promotes cell differentiation and stimulates lipid production in keratinocyte cultures.

EP-A-1 216 692 discloses the use of 2-methyl-2-(β-carboxyethyl)chroman derivatives in cosmetic compositions. The said compositions are particularly suitable for prophylaxis against ageing processes of skin and hair and for prophylaxis against dry skin, wrinkle formation and pigment defects.

Compositions for topical application which comprise chromone derivatives, such as, for example, chromone, 7-hydroxychromone, 7-methoxychromone, 5,7-dihydroxy-2-methylchromone, 3-methyl-2-butenyloxychromone, 3-acetyl-5,7-dihydroxy-2-methylchromone, 5-hydroxychromone, n-pentyl 7-methoxychromone-2-carboxylate, n-undecyl 5-methoxychromone-2-carboxylate, 5-hydroxy-7-methoxy-2-methylchromone, 7-methoxychromone-2-carboxylic acid, n-pentylchromone-2-carboxylic acid, 5-methoxychromone and chromone-2-carboxylic acid, are disclosed in Japanese patent application JP 05/301813. The chromone derivatives act as skin-tolerated tyrosinase inhibitors which reduce hyperpigmentation of the skin.

Japanese patent application JP 09/188,608 discloses the use of substituted chromone derivatives, such as, in particular, 5,7-dihydroxychromones, 7-methoxychromones, 5-hydroxy-7-methoxy-2-methylchromone and 5-hydroxy-2-methylchromone, as active ingredient against grey hair. The action here is attributed to activation of the coloured pigment-forming cells and the increase in melanogenesis.

A composition against skin ageing comprising chromone derivatives which are substituted in the 2-position by $C_{1-15}$-alkyl and have H, OH or alkoxy substitution in the 7-position, in combination with aminopropanol derivatives is disclosed in JP 10/194,919.

Cosmetic compositions which comprise substituted chromone derivatives, such as, for example, 2-(1-ethylpentyl)chromone, 5,7-dihydroxychromones, 7-methoxychromones, 5-hydroxy-7-methoxy-2-methylchromone and 5-hydroxy-2-methylchromone, and aromatic compounds having a melting point of −10° C. or above are disclosed in JP 10/114,640. The chromone derivative here simplifies incorporation of the aromatic compound into the cosmetic formulation.

The compounds of the formula I are typically employed in accordance with the invention in amounts of from 0.01 to 20% by weight, preferably in amounts of from 0.1% by weight to 10% by weight and particularly preferably in amounts of from 1 to 8% by weight. The person skilled in the art has absolutely no difficulties in selecting the amount correspondingly depending on the intended action of the composition.

The protective action against oxidative stress or against the effect of free radicals can thus be further improved if the compositions comprise one or more further antioxidants, where the person skilled in the art has absolutely no difficulties in selecting antioxidants having a suitably fast or time-delayed action.

In a preferred embodiment of the present invention, at least one further skin-care ingredient is one or more antioxidants and/or vitamins.

For the above-mentioned reasons, it is particularly preferred here for the composition to comprise no retinol derivative.

There are many proven substances known from the specialist literature which can be used as antioxidants, for example amino acids (for example glycine, histidine, tyrosine, tryptophan) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (for example buthionine sulfoximines, homocysteine sulfoximine, buthionine sulfones, penta-, hexa- and heptathionine sulfoximine) in very low tolerated doses (for example pmol to μmol/kg), furthermore (metal) chelating agents (for example α-hydroxy fatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof, vitamin C and derivatives (for example ascorbyl palmitate, magnesium ascorbyl phosphate, ascorbyl acetate), tocopherols and derivatives (for example vitamin E acetate), and coniferyl benzoate of benzoin resin, rutinic acid and derivatives thereof, α-glycosylrutin, ferulic acid, furfurylideneglucitol, carnosine, butylhydroxytoluene, butylhydroxyanisole, nordihydroguaiaretic acid, trihydroxybutyrophenone, quercetin, uric acid and derivatives thereof, mannose and derivatives thereof, zinc and derivatives thereof (for example ZnO, $ZnSO_4$), selenium and derivatives thereof (for example selenomethionine), stilbenes and derivatives thereof (for example stilbene oxide, trans-stilbene oxide).

Mixtures of antioxidants are likewise suitable for use in the cosmetic compositions according to the invention. Known and commercial mixtures are, for example, mixtures comprising, as active ingredients, lecithin, L-(+)-ascorbyl palmitate and citric acid (for example Oxynex® AP), natural tocopherols, L-(+)-ascorbyl palmitate, L-(+)-ascorbic acid and citric acid (for example Oxynex® K LIQUID), tocopherol extracts from natural sources, L-(+)-ascorbyl palmitate, L-(+)-ascorbic acid and citric acid (for example Oxynexe L LIQUID), DL-α-tocopherol, L-(+)-ascorbyl palmitate, citric acid and lecithin (for example Oxynex® LM) or butylhydroxytoluene (BHT), L-(+)-ascorbyl palmitate and citric acid (for example Oxynex® 2004). Anti-oxidants of this type are usually employed with compounds of the formula I in compositions of this type in ratios in the range from 1000:1 to 1:1000, preferably in amounts of from 100:1 to 1.100.

The compositions according to the invention may comprise vitamins as further ingredients. The cosmetic compositions according to the invention preferably comprise vitamins and vitamin derivatives selected from vitamin B, thiamine chloride hydrochloride (vitamin Bi), riboflavin (vitamin $B_2$), nicotinamide, vitamin C (ascorbic acid), vitamin D, ergocalciferol (vitamin $D_2$), vitamin E, DL-α-tocopherol, tocopherol E acetate, tocopherol hydrogensuccinate, vitamin $K_1$, esculin (vitamin P active ingredient), thiamine (vitamin $B_1$), nicotinic acid (niacin), pyridoxine, pyridoxal, pyridoxamine (vitamin $B_6$), pantothenic acid, biotin, folic acid and cobalamine (vitamin $B_{12}$), particularly preferably vitamin C and derivatives thereof, DL-α-tocopherol, tocopherol E acetate, nicotinic acid, pantothenic acid and biotin. Vitamins are usually employed here with compounds of the formula I in ratios in the range from 1000:1 to 1:1000, preferably in amounts of from 100:1 to 1:100.

Of the phenols having an antioxidative action, the polyphenols, some of which are naturally occurring, are of particular interest for applications in the pharmaceutical, cosmetic or nutrition sector. For example, the flavonoids or bioflavonoids, which are principally known as plant dyes, frequently have an antioxidant potential. K. Lemanska, H. Szymusiak, B. Tyrakowska, R. Zielinski, I. M. C. M. Rietjens; Current Topics in Biophysics 2000, 24(2), 101-108, are concerned with effects of the substitution pattern of mono- and dihydroxyflavones. It is observed therein that dihydroxyflavones containing an OH group adjacent to the keto function or OH groups in the 3',4'- or 6,7- or 7,8-position have antioxidative properties, while other mono- and dihydroxyflavones in some cases do not have antioxidative properties.

Quercetin (cyanidanol, cyanidenolon 1522, meletin, sophoretin, ericin, 3,3',4',5,7-pentahydroxyflavone) is frequently mentioned as a particularly effective antioxidant (for example C. A. Rice-Evans, N. J. Miller, G. Paganga, Trends in Plant Science 1997, 2(4), 152-159). K. Lemanska, H. Szymusiak, B. Tyrakowska, R. Zielinski, A. E. M. F. Soffers, I. M. C. M. Rietjens; Free Radical Biology&Medicine 2001, 31(7), 869-881; have investigated the pH dependence of the antioxidant action of hydroxyflavones. Quercetin exhibits the greatest activity amongst the structures investigated over the entire pH range.

Suitable antioxidants are furthermore compounds of the formula II

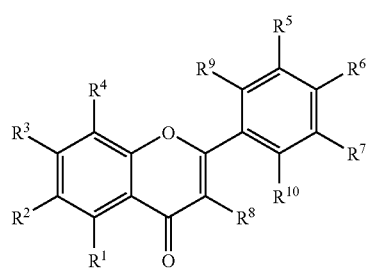

where $R^1$ to $R^{10}$ may be identical or different and are selected from
H
$OR^{11}$
straight-chain or branched $C_1$- to $C_{20}$-alkyl groups,
straight-chain or branched $C_3$- to $C_{20}$-alkenyl groups,
straight-chain or branched $C_1$- to $C_{20}$-hydroxyalkyl groups, where the hydroxyl group may be bonded to a primary or secondary carbon atom of the chain and furthermore the alkyl chain may also be interrupted by oxygen, and/or
$C_3$- to $C_{10}$-cycloalkyl groups and/or $C_3$- to $C_{12}$-cycloalkenyl groups, where the rings may each also be bridged by —$(CH_2)_n$— groups, where n=1 to 3,
where all $OR^{11}$ are, independently of one another,
OH
straight-chain or branched $C_1$- to $C_{20}$-alkoxy groups,
straight-chain or branched $C_3$- to $C_{20}$-alkenyloxy groups,
straight-chain or branched $C_1$- to $C_{20}$-hydroxyalkoxy groups, where the hydroxyl group(s) may be bonded to a primary or secondary carbon atom of the chain and furthermore the alkyl chain may also be interrupted by oxygen, and/or
$C_3$- to $C_{10}$-cycloalkoxy groups and/or $C_3$- to $C_{12}$-cycloalkenyloxy groups, where the rings may each also be bridged by —$(CH_2)_n$— groups, where n=1 to 3, and/or
mono- and/or oligoglycosyl radicals, with the proviso that at least 4 radicals from $R^1$ to $R^7$ are OH and that the molecule contains at least two pairs of adjacent —OH groups,
or $R^2$, $R^5$ and $R^6$ are OH and the radicals $R^1$, $R^3$, $R^4$ and $R^{7-10}$ are H, as described in the earlier German patent application DE 10244282.7.

Besides the advantages mentioned above, the advantages of the compositions according to the invention comprising at least one antioxidant here are, in particular, the antioxidant action and the good skin tolerability. In addition, the compounds described here are preferably colourless or have only a weak colour and thus only result in slight discoloration of the comto positions, or none at all. Of particular advantage is the particular action profile of the compounds of the formula II, which is evident in the DPPH assay in a high capacity for scavenging free radicals ($EC_{50}$), a time-delayed action ($T_{EC50}$>120 min) and thus a moderate to high anti-free-radical efficiency (AE). In addition, the compounds of the formula I combine antioxidative properties with UV absorption in the UV-A and/or UV-B region in the molecule. Preference is therefore also given to compositions comprising at least one compound of the formula II which is characterised in that at least two adjacent radicals of the radicals $R^1$ to $R^4$ are OH and at least two adjacent radicals of the radicals $R^5$ to $R^7$ are OH. Particularly preferred compositions comprise at least one compound of the formula II which is characterised in that at least three adjacent radicals of the radicals $R^1$ to $R^4$ are OH, preferably with the radicals $R^1$ to $R^3$ being OH.

In order that the compounds of the formula I are able to develop their positive action as free-radical scavengers on the skin particularly well, it may be preferred to allow the compounds of the formula I to penetrate into deeper skin layers. Several possibilities are available for this purpose. Firstly, the compounds of the formula I can have an adequate lipophilicity in order to be able to penetrate through the outer skin layer into epidermal layers. As a further possibility, corresponding transport agents, for example liposomes, which enable transport of the compounds of the formula I through the outer skin layers may also be provided in the composition. Finally, systemic transport of the compounds of the formula I is also conceivable. The composition is then designed, for example, in such a way that it is suitable for oral administration.

It is also advantageous to administer the compounds of the formula II in encapsulated form, for example as cellulose or chitin capsules, in gelatine or wax matrices or encapsulated with cyclodextrins.

It is assumed that the preferred compounds of the formula I also act as enzyme inhibitors. They presumably inhibit protein kinases, elastase, aldose reductase and hyaluronidase, and therefore enable the intactness of the basic substance of vascular sheaths to be maintained. Furthermore, they presumably inhibit non-specifically catechol O-methyl transferase, causing the amount of available catecholamine and thus the vascular strength to be increased. Furthermore, they are thought to inhibit AMP phosphodiesterase, giving the substances potential for inhibiting thrombocyte aggregation.

Owing to these properties, the compositions according to the invention are, in general, suitable for immune protection and for the protection of DNA and RNA. In particular, the compositions are suitable for the protection of DNA and RNA against oxidative attack, against free radicals and against damage due to radiation, in particular UV radiation. A further advantage of the compositions according to the invention is cell protection, in particular protection of Langerhans cells against damage due to the above-mentioned influences. All these uses and the use of the compounds of the formula I for the preparation of compositions which can be employed correspondingly are expressly also a subject-matter of the present invention.

In particular, preferred compositions according to the invention are also suitable for the treatment of skin diseases associated with a defect in keratinisation which affects differentiation and cell proliferation, in particular for the treatment of acne vulgaris, acne comedonica, polymorphic acne, acne rosaceae, nodular acne, acne conglobata, age-induced acne, acne which arises as a side effect, such as acne solaris, medicament-induced acne or acne professionalis, for the treatment of other defects in keratinisation, in particular ichthyosis, ichthyosiform states, Darier's disease, keratosis palmoplantaris, leucoplasia, leucoplasiform states, herpes of the skin and mucous membrane (buccal) (lichen), for the treatment of other skin diseases associated with a defect in keratinisation and which have an inflammatory and/or immunoallergic component and in particular all forms of psoriasis which affect the skin, mucous membranes and fingers and toenails, and psoriatic rheumatism and skin atopy, such as eczema or respiratory atopy, or hypertrophy of the gums, it furthermore being possible for the compounds to be used for some inflammations which are not associated with a defect in keratinisation, for the treatment of all benign or malignant excrescence of the dermis or epidermis, which may be of viral origin, such as verruca vulgaris, verruca plana, epidermodysplasia verruciformis, oral papillomatosis, papillomatosis florida, and excrescence which may be caused by UV radiation, in particular epithelioma baso-cellulare and epithelioma spinocellulare, for the treatment of other skin diseases, such as dermatitis bullosa and diseases affecting the collagen, for the treatment of certain eye diseases, in particular corneal diseases, for overcoming or combating light-induced skin ageing associated with ageing, for reducing pigmentation and keratosis actinica and for the treatment of all diseases associated with normal ageing or light-induced ageing, for the prevention or healing of wounds/scars of atrophy of the epidermis and/or dermis caused by locally or systemically applied corticosteroids and all other types of skin atrophy, for the prevention or treatment of defects in wound healing, for the prevention or elimination of stretch marks caused by pregnancy or for the promotion of wound healing, for combating defects in tallow production, such as hyperseborrhoea in acne or simple seborrhoea, for combating or preventing cancer-like states or pre-carcinogenic states, in particular promyelocytic leukaemia, for the treatment of inflammatory diseases, such as arthritis, for the treatment of all virus-induced diseases of the skin or other areas of the body, for the prevention or treatment of alopecia, for the treatment of skin diseases or diseases of other areas of the body with an immunological component, for the treatment of cardiovascular diseases, such as arteriosclerosis or hypertension, and of non-insulin-dependent diabetes, and for the treatment of skin problems caused by UV radiation.

Compositions which are particularly preferred in accordance with the invention also comprise UV filters besides the compounds of the formula I.

Use of the dibenzoylmethane derivatives, which are particularly preferred as UV-A filters, in combination with the compounds of the formula I gives rise to a further additional advantage: the UV-sensitive dibenzoylmethane derivatives are additionally stabilised by the presence of the compounds of the formula I. The present invention therefore furthermore relates to the use of the compounds of the formula I for the stabilisation of dibenzoylmethane derivatives in compositions.

In principle, all UV filters are suitable for combination with the compounds of the formula I. Particular preference is given to UV filters whose physiological acceptability has already been demonstrated. Both for UVA and UVB filters, there are many proven substances which are known from the specialist literature, for example:

benzylidenecamphor derivatives, such as 3-(4'-methylbenzylidene)-dl-camphor (for example Eusolex® 6300), 3-benzylidenecamphor (for example Mexoryl® SD), polymers of N-{(2 and 4)-[(2-oxoborn-3-ylidene)methyl]-benzyl}acrylamide (for example Mexoryl® SW), N,N,N-trimethyl-4-(2-oxoborn-3-ylidenemethyl)anilinium methylsulfate (for example Mexoryl® SK) or (2-oxoborn-3-ylidene) toluene-4-sulfonic acid (for example Mexoryl® SL), benzoyl- or dibenzoylmethanes, such as 1-(4-tert-butylphenyl)-3-(4-methoxyphenyl)propane-1,3-dione (for example Eusolex® 9020) or 4-isopropyldibenzoylmethane (for example Eusolex® 8020), benzophenones, such as 2-hydroxy-4-methoxybenzophenone (for example Eusolex® 4360) or 2-hydroxy-4-methoxybenzophenone-5-sulfonic acid and its sodium salt (for example Uvinul® MS-40), methoxycinnamic acid esters, such as octyl methoxycinnamate (for example Eusolex® 2292) or isopentyl 4-methoxycinnamate, for example as a mixture of the isomers (for example Neo Heliopan® E 1000), salicylate derivatives, such as 2-ethylhexyl salicylate (for example Eusolex® OS), 4-isopropylbenzyl salicylate (for example Megasol®) or 3,3,5-trimethylcyclohexyl salicylate (for example Eusolex® HMS), 4-aminobenzoic acid and derivatives, such as 4-aminobenzoic acid, 2-ethylhexyl 4-(dimethylamino)benzoate (for example Eusolex® 6007) or ethoxylated ethyl 4-aminobenzoate (for example Uvinul® P25), phenylbenzimidazolesulfonic acids, such as 2-phenylbenzimidazole-5-sulfonic acid and potassium, sodium and triethanolamine salts thereof (for example Eusolex® 232), 2,2-(1,4-phenylene)bisbenzimidazole-4,6-disulfonic acid and salts thereof (for example Neoheliopan® AP) or 2,2-(1,4-phenylene)bisbenzimidazole-6-sulfonic acid;

and further substances, such as 2-ethylhexyl 2-cyano-3,3-diphenylacrylate (for example Eusolex® OCR), 3,3'-(1,4-phenylenedimethylene)bis(7,7-dimethyl-2-oxobicyclo[2.2.1]-hept-1-ylmethanesulfonic acid and salts thereof (for example Mexoryl® SX), 2,4,6-trianilino-(p-carbo-2'-ethylhexyl-1'-oxy)-1,3,5-triazine (for example Uvinul® T 150) and hexyl 2-(4-diethylamino-2-hydroxybenzoyl)benzoate (for example Uvinul® UVA Plus, BASF).

The compounds mentioned in the list should only be regarded as examples. It is of course also possible to use other UV filters.

These organic UV filters are generally incorporated into cosmetic formulations in an amount of from 0.5 to 10 percent by weight, preferably 1-8%.

Further suitable organic UV filters are, for example, 2-(2H-benzotriazol-2-yl)-4-methyl-6-(2-methyl-3-(1,3,3,3-tetramethyl-1-(trimethylsilyloxy)disiloxanyl)propyl)phenol (for example Silatrizole®), 2-ethylhexyl 4,4'-[(6-[4-((1,1-dimethylethyl)aminocarbonyl)phenylamino]-1,3,5-triazine-2,4-diyl)diimino]bis(benzoate) (for example Uvasorb® HEB), α-(trimethylsilyl)-ω-[trimethylsilyl)oxy]poly[oxy(dimethyl [and about 6% of methyl[2-[p-[2,2-bis(ethoxycarbonyl) vinyl]phenoxy]-1-methyleneethyl] and approximately 1.5% of methyl[3-[p-[2,2-bis(ethoxycarbonyl)vinyl]-phenoxy]propenyl] and from 0.1 to 0.4% of (methylhydrogen] silylene]] (n≈60) (CAS No. 207 574-74-1)

2,2'-methylenebis(6-(2H-benzotriazol-2-yl)-4-(1,1,3,3-tetramethylbutyl)-phenol) (CAS No. 103 597-45-1)

2,2'-(1,4-phenylene)bis(1H-benzimidazole-4,6-disulfonic acid, mono-sodium salt) (CAS No. 180 898-37-7), 2,4-bis{[4-(2-ethylhexyloxy)-2-hydroxyl]phenyl}-6-(4-methoxyphenyl)-1,3,5-triazine (CAS No. 103 597-45-, 187 393-00-6) and 2-ethylhexyl 4,4'-[(6-[4-((1,1-dimethylethyl)aminocarbonyl)phenylamino]-1,3,5-triazine-2,4-diyl)diimino]bis (benzoate) (for example Uvasorb® HEB).

Further suitable UV filters are also methoxyflavones corresponding to the earlier German patent application DE 10232595.2.

Organic UV filters are generally incorporated into cosmetic formulations in an amount of from 0.5 to 20 percent by weight, preferably 1-15%.

Conceivable inorganic UV filters are those from the group consisting of titanium dioxides, such as, for example, coated titanium dioxide (for example Eusolex® T-2000, Eusolex® T-AQUA), zinc oxides (for example Sachtotec®), iron oxides and also cerium oxides. These inorganic UV filters are generally incorporated into cosmetic compositions in an amount of from 0.5 to 20 percent by weight, preferably 2-10%.

Preferred compounds having UV-filtering properties are 3-(4'-methylbenzylidene)-dl-camphor, 1-(4-tert-butylphenyl)-3-(4-methoxyphenyl)propane-1,3-dione, 4-isopropyldibenzoylmethane, 2-hydroxy-4-methoxybenzophenone, octyl methoxycinnamate, 3,3,5-trimethylcyclohexyl salicylate, 2-ethylhexyl 4-(dimethylamino)benzoate, 2-ethylhexyl 2-cyano-3,3-diphenylacrylate, 2-phenylbenzimidazole-5-sulfonic acid and its potassium, sodium and triethanolamine salts.

Through combination of one or more compounds of the formula I with further UV filters, the protective action against harmful influences of UV radiation can be optimised.

Optimised compositions may comprise, for example, the combination of the organic UV filters 4'-methoxy-6-hydroxyflavone with 1-(4-tert-butylphenyl)-3-(4-methoxyphenyl) propane-1,3-dione and 3-(4'-methylbenzylidene)-dl-camphor. This combination gives rise to broad-band protection, which can be supplemented by the addition of inorganic UV filters, such as titanium dioxide microparticles.

All the said UV filters can also be employed in encapsulated form. In particular, it is advantageous to employ organic UV filters in encapsulated form. In detail, the following advantages arise:

The hydrophilicity of the capsule wall can be set independently of the solubility of the UV filter. Thus, for example, it is also possible to incorporate hydrophobic UV filters into purely aqueous compositions. In addition, the oily impression on application of the composition comprising hydrophobic UV filters, which is frequently regarded as unpleasant, is suppressed.

Certain UV filters, in particular dibenzoylmethane derivatives, exhibit only reduced photostability in cosmetic compositions. Encapsulation of these filters or compounds which impair the photostability of these filters, such as, for example, cinnamic acid derivatives, enables the photostability of the entire composition to be increased.

Skin penetration by organic UV filters and the associated potential for irritation on direct application to the human skin is repeatedly being discussed in the literature. The encapsulation of the corresponding substances which is proposed here suppresses this effect.

In general, encapsulation of individual UV filters or other ingredients enables composition problems caused by the interaction of individual composition constituents with one another, such as crystallisation processes, precipitation and agglomerate formation, to be avoided since the interaction is suppressed.

It is therefore preferred in accordance with the invention for one or more of the above-mentioned UV filters to be in encapsulated form. It is advantageous here for the capsules to be so small that they cannot be viewed with the naked eye. In order to achieve the above-mentioned effects, it is furthermore necessary for the capsules to be sufficiently stable and the encapsulated active ingredient (UV filter) only to be released to the environment to a small extent, or not at all.

Suitable capsules can have walls of inorganic or organic polymers. For example, U.S. Pat. No. 6,242,099 B1 describes the production of suitable capsules with walls of chitin, chitin derivatives or polyhydroxylated polyamines. Capsules which can particularly preferably be employed in accordance with the invention have walls which can be obtained by a sol-gel process, as described in the applications WO 00/09652, WO 00/72806 and WO 00/71084. Preference is again given here to capsules whose walls are built up from silica gel (silica; undefined silicon oxide hydroxide). The production of corresponding capsules is known to the person skilled in the art, for example from the cited patent applications, whose contents expressly also belong to the subject-matter of the present application.

The capsules are preferably present in compositions according to the invention in amounts which ensure that the encapsulated UV filters are present in the composition in the above-indicated amounts.

The skin-protecting or skin-care active ingredients can in principle be any active ingredients known to the person skilled in the art.

In an embodiment of the present invention, particularly preferred active ingredients are pyrimidinecarboxylic acids and/or aryl oximes.

Pyrimidinecarboxylic acids occur in halophilic microorganisms and play a role in osmoregulation of these organisms (E. A. Galinski et al., Eur. J. Biochem., 149 (1985) pages 135-139). Of the pyrimidinecarboxylic acids, particular mention should be made here of ectoine ((S)-1,4,5,6-tetrahydro-2-methyl-4-pyrimidinecarboxylic acid) and hydroxyectoine ((SS)-1,4,5,6-tetrahydro-5-hydroxy-2-methyl-4-pyrimidinecarboxylic acid) and derivatives thereof. These compounds stabilise enzymes and other biomolecules in aqueous solutions and organic solvents. Furthermore, they stabilise, in particular, enzymes against denaturing conditions, such as salts, extreme pH values, surfactants, urea, guanidinium chloride and other compounds.

Ectoine and ectoine derivatives, such as hydroxyectoine, can advantageously be used in medicaments. In particular, hydroxyectoine can be employed for the preparation of a medicament for the treatment of skin diseases. Other areas of application of hydroxyectoine and other ectoine derivatives are typically in areas in which, for example, trehalose is used as additive. Thus, ectoine derivatives, such as hydroxyectoine, can be used as protectant in dried yeast and bacteria cells. Pharmaceutical products, such as non-glycosylated, pharmaceutically active peptides and proteins, for example t-PA, can also be protected with ectoine or its derivatives.

Of the cosmetic applications, particular mention should be made of the use of ectoine and ectoine derivatives for the care of aged, dry or irritated skin. Thus, European patent application EP-A-0 671 161 describes, in particular, that ectoine and hydroxyectoine are employed in cosmetic compositions, such as powders, soaps, surfactant-containing cleansing products, lipsticks, rouge, make-ups, care creams and sunscreen compositions.

Preference is given here to the use of a pyrimidinecarboxylic acid of the following formula II

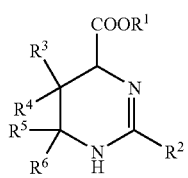

in which $R^1$ is a radical H or C1-8-alkyl, $R^2$ is a radical H or C1-4-alkyl, and $R^3$, $R^4$, $R^5$ and $R^6$ are each, independently of one another, a radical from the group consisting of H, OH, $NH_2$ and C1-4-alkyl. Preference is given to the use of pyrimidinecarboxylic acids in which $R^2$ is a methyl or ethyl group, and $R^1$ or $R^5$ and $R^6$ are H. Particular preference is given to the use of the pyrimidinecarboxylic acids ectoine ((S)-1,4,5,6-tetrahydro-2-methyl-4-pyrimidinecarboxylic acid) and hydroxyectoine ((S,S)-1,4,5,6-tetrahydro-5-hydroxy-2-methyl-4-pyrimidinecarboxylic acid). The compositions according to the invention preferably comprise pyrimidinecarboxylic acids of this type in amounts of up to 15% by weight. The pyrimidinecarboxylic acids are preferably employed here in ratios of from 100:1 to 1:100 with respect to the compounds of the formula I, with ratios in the range from 1:10 to 10:1 being particularly preferred.

Of the aryl oximes, preference is given to the use of 2-hydroxy-5-methyllaurophenone oxime, which is also known as HMLO, LPO or F5. Its suitability for use in cosmetic compositions is disclosed, for example, in DE-A-41 16 123. Compositions which comprise 2-hydroxy-5-methyllaurophenone oxime are accordingly suitable for the treatment of skin diseases which are accompanied by inflammation. It is known that compositions of this type can be used, for example, for the therapy of psoriasis, various forms of eczema, irritative and toxic dermatitis, UV dermatitis and further allergic and/or inflammatory diseases of the skin and integumentary appendages. Compositions according to the invention which, in addition to the compound of the formula I, additionally comprise an aryl oxime, preferably 2-hydroxy-5-methyllaurophenone oxime, exhibit surprising anti-inflammatory suitability. The compositions here preferably comprise from 0.01 to 10% by weight of the aryl oxime, it being particularly preferred for the composition to comprise from 0.05 to 5% by weight of aryl oxime.

All compounds or components which can be used in the compositions are either known or commercially available or can be synthesised by known processes. The preparation of the novel compounds of the formula I is described below.

The one or more compounds of the formula I can be incorporated into cosmetic or dermatological compositions in the customary manner. Suitable compositions are those for external use, for example in the form of a cream, lotion or gel or as a solution which can be sprayed onto the skin, Suitable for internal use are administration forms such as capsules, coated tablets, powders, tablet solutions or solutions.

Use forms of the compositions according to the invention that may be mentioned are, for example, solutions, suspensions, emulsions, PIT emulsions, pastes, ointments, gels, creams, lotions, powders, soaps, surfactant-containing cleansing preparations, oils, aerosols and sprays. Examples of other use forms are sticks, shampoos and shower compositions. Any desired customary carriers, assistants and, if desired, further active ingredients may be added to the composition.

Preferred assistants originate from the group consisting of preservatives, antioxidants, stabilisers, solubilisers, vitamins, colorants and odour improvers.

Ointments, pastes, creams and gels may comprise the customary carriers, for example animal and vegetable fats, waxes, paraffins, starch, tragacanth, cellulose derivatives, polyethylene glycols, silicones, bentonites, silica, talc and zinc oxide, or mixtures of these substances.

Powders and sprays may comprise the customary carriers, for example lactose, talc, silica, aluminium hydroxide, calcium silicate and polyamide powder, or mixtures of these substances. Sprays may additionally comprise the customary propellants, for example chlorofluorocarbons, propane/butane or dimethyl ether.

Solutions and emulsions may comprise the customary carriers, such as solvents, solubilisers and emulsifiers, for example water, ethanol, isopropanol, ethyl carbonate, ethyl acetate, benzyl alcohol, benzyl benzoate, propylene glycol, 1,3-butyl glycol, oils, in particular cottonseed oil, peanut oil, wheatgerm oil, olive oil, castor oil and sesame oil, glycerol fatty acid esters, polyethylene glycols and fatty acid esters of sorbitan, or mixtures of these substances.

Suspensions may comprise the customary carriers, such as liquid diluents, for example water, ethanol or propylene glycol, suspending agents, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

Soaps may comprise the customary carriers, such as alkali metal salts of fatty acids, salts of fatty acid monoesters, fatty acid protein hydrolysates, isethionates, lanolin, fatty alcohol, vegetable oils, plant extracts, glycerol, sugars, or mixtures of these substances.

Surfactant-containing cleansing products may comprise the customary carriers, such as salts of fatty alcohol sulfates, fatty alcohol ether sulfates, sulfosuccinic acid monoesters, fatty acid protein hydrolysates, isethionates, imidazolinium derivatives, methyl taurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerol fatty acid esters, or mixtures of these substances.

Face and body oils may comprise the customary carriers, such as synthetic oils, such as fatty acid esters, fatty alcohols, silicone oils, natural oils, such as vegetable oils and oily plant extracts, paraffin oils or lanolin oils, or mixtures of these substances.

Further typical cosmetic use forms are also lipsticks, lip-care sticks, mascara, eyeliner, eye-shadow, rouge, powder make-up, emulsion make-up and wax make-up, and sunscreen, pre-sun and after-sun preparations.

The preferred composition forms according to the invention include, in particular, emulsions.

Emulsions according to the invention are advantageous and comprise, for example, the said fats, oils, waxes and other fatty substances, as well as water and an emulsifier, as usually used for a composition of this type.

The lipid phase may advantageously be selected from the following group of substances:

mineral oils, mineral waxes;

oils, such as triglycerides of capric or caprylic acid, furthermore natural oils, such as, for example, castor oil;

fats, waxes and other natural and synthetic fatty substances, preferably esters of fatty acids with alcohols having a low carbon number, for example with isopropanol, propylene glycol or glycerol, or esters of fatty alcohols with alkanoic acids having a low carbon number or with fatty acids;

silicone oils, such as dimethylpolysiloxanes, diethylpolysiloxanes, diphenylpolysiloxanes and mixed forms thereof.

For the purposes of the present invention, the oil phase of the emulsions, oleogels or hydrodispersions or lipodispersions is advantageously selected from the group consisting of esters of saturated and/or unsaturated, branched and/or unbranched alkanecarboxylic acids having a chain length of from 3 to 30 carbon atoms and saturated and/or unsaturated, branched and/or unbranched alcohols having a chain length of from 3 to 30 carbon atoms, or from the group consisting of esters of aromatic carboxylic acids and saturated and/or unsaturated, branched and/or unbranched alcohols having a chain length of from 3 to 30 carbon atoms. Ester oils of this type can then advantageously be selected from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic and natural mixtures of esters of this type, for example jojoba oil.

The oil phase may furthermore advantageously be selected from the group consisting of branched and unbranched hydrocarbons and waxes, silicone oils, dialkyl ethers, or the group consisting of saturated and unsaturated, branched and unbranched alcohols, and fatty acid triglycerides, specifically the triglycerol esters of saturated and/or unsaturated, branched and/or unbranched alkanecarboxylic acids having a chain length of from 8 to 24, in particular 12-18, carbon atoms. The fatty acid triglycerides may advantageously be selected, for example, from the group consisting of synthetic, semi-synthetic and natural oils, for example olive oil, sunflower oil, soya oil, peanut oil, rapeseed oil, almond oil, palm oil, coconut oil, palm kernel oil and the like.

Any desired mixtures of oil and wax components of this type may also advantageously be employed for the purposes of the present invention. It may also be advantageous to employ waxes, for example cetyl palmitate, as the only lipid component of the oil phase.

The oil phase is advantageously selected from the group consisting of 2-ethylhexyl isostearate, octyldodecanol, isotridecyl isononanoate, isoeicosane, 2-ethylhexyl cocoate, $C_{12-15}$-alkyl benzoate, caprylicicapric acid triglyceride and dicapryl ether.

Particularly advantageous are mixtures of $C_{12-15}$-alkyl benzoate and 2-ethylhexyl isostearate, mixtures of $C_{12-15}$-alkyl benzoate and isotridecyl isononanoate, as well as mixtures of $C_{12-15}$-alkyl benzoate, 2-ethylhexyl isostearate and isotridecyl isononanoate.

Of the hydrocarbons, paraffin oil, squalane and squalene may advantageously be used for the purposes of the present invention.

Furthermore, the oil phase may also advantageously have a content of cyclic or linear silicone oils or consist entirely of oils of this type, although it is preferred to use an additional content of other oil-phase components in addition to the silicone oil or the silicone oils.

The silicone oil to be used in accordance with the invention is advantageously cyclomethicone (octamethylcyclotetrasiloxane). However, it is also advantageous for the purposes of the present invention to use other silicone oils, for example hexamethylcyclotrisiloxane, polydimethylsiloxane or poly(methylphenylsiloxane).

Also particularly advantageous are mixtures of cyclomethicone and isotridecyl isononanoate and of cyclomethicone and 2-ethylhexyl isostearate.

The aqueous phase of the compositions according to the invention optionally advantageously comprises alcohols, diols or polyols having a low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, furthermore alcohols having a low carbon number, for example ethanol, isopropanol, 1,2-propanediol or glycerol, and, in particular, one or more thickeners, which may advantageously be selected from the group consisting of silicon dioxide, aluminium silicates, polysaccharides and derivatives thereof, for example hyaluronic acid, xanthan gum, hydroxypropylmethylcellulose, particularly advantageously from the group consisting of the polyacrylates, preferably a polyacrylate from the group consisting of the so-called Carbopols, for example Carbopol grades 980, 981, 1382, 2984 or 5984, in each case individually or in combination.

In particular, mixtures of the above-mentioned solvents are used. In the case of alcoholic solvents, water may be a further constituent.

Emulsions according to the invention are advantageous and comprise, for example, the said fats, oils, waxes and other fatty substances, as well as water and an emulsifier, as usually used for a formulation of this type.

In a preferred embodiment, the compositions according to the invention comprise hydrophilic surfactants.

The hydrophilic surfactants are preferably selected from the group consisting of the alkylglucosides, acyl lactylates, betaines and coconut amphoacetates.

The alkylglucosides are themselves advantageously selected from the group consisting of the alkylglucosides which are distinguished by the structural formula

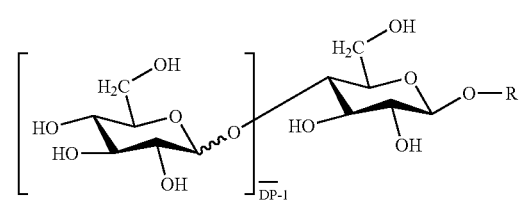

where R is a branched or unbranched alkyl radical having from 4 to 24 carbon atoms, and where $\overline{DP}$ denotes a mean degree of glucosylation of up to 2.

The value $\overline{DP}$ represents the degree of glucosidation of the alkylglucosides used in accordance with the invention and is defined as $$\overline{DP} = \frac{p_1}{100} \cdot 1 + \frac{p_2}{100} \cdot 2 + \frac{p_3}{100} \cdot 3 + \ldots = \sum \frac{p_i}{100} \cdot i$$

in which $p_1, p_2, p_3 \ldots p_i$ represent the proportion of mono-, di-, tri- . . . i-fold glucosylated products in percent by weight. Products which are advantageous according to the invention are those having degrees of glucosylation of 1-2, particularly advantageously of from 1.1 to 1.5, very particularly advantageously of 1.2-1.4, in particular of 1.3.

The value DP takes into account the fact that alkylglucosides are generally, as a consequence of their preparation, in the form of mixtures of mono- and oligoglucosides. A relatively high content of monoglucosides, typically in the order of 40-70% by weight, is advantageous in accordance with the invention.

Alkylglycosides which are particularly advantageously used for the purposes of the invention are selected from the group consisting of octyl glucopyranoside, nonyl glucopyranoside, decyl glucopyranoside, undecyl glucopyranoside, dodecyl glucopyranoside, tetradecyl glucopyranoside and hexadecyl glucopyranoside.

It is likewise advantageous to employ natural or synthetic raw materials and assistants or mixtures which are distinguished by an effective content of the active ingredients used in accordance with the invention, for example Plantaren® 1200 (Henkel KGaA), Oramix® NS 10 (Seppic).

The acyllactylates are themselves advantageously selected from the group consisting of the substances which are distinguished by the structural formula

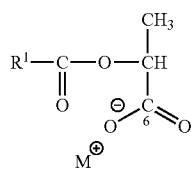

where $R^1$ is a branched or unbranched alkyl radical having from 1 to 30 carbon atoms, and M⁺ is selected from the group consisting of the alkali metal ions and the group consisting of ammonium ions which are substituted by one or more alkyl and/or one or more hydroxyalkyl radicals, or corresponds to half an equivalent of an alkaline earth metal ion.

For example, sodium isostearyl lactylate, for example the product Pathionic® ISL from the American Ingredients Company, is advantageous.

The betaines are advantageously selected from the group consisting of the substances which are distinguished by the structural formula

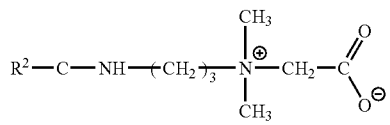

where $R^2$ is a branched or unbranched alkyl radical having from 1 to 30 carbon atoms.

$R^2$ is particularly advantageously a branched or unbranched alkyl radical having from 6 to 12 carbon atoms.

For example, capramidopropylbetaine, for example the product Tego® Betain 810 from Th; Goldschmidt AG; is advantageous.

A coconut amphoacetate which is advantageous for the purposes of the invention is, for example, sodium coconut amphoacetate, as available under the name Miranol® Ultra C32 from Miranol Chemical Corp.

The compositions according to the invention are advantageously characterised in that the hydrophilic surfactant(s) is (are) present in concentrations of 0.01-20% by weight, preferably 0.05-10% by weight, particularly preferably 0.1-5% by weight, in each case based on the total weight of the composition.

For use, the cosmetic and dermatological compositions are applied in sufficient amount to the skin and/or hair in the usual manner for cosmetics.

Cosmetic and dermatological compositions according to the invention may exist in various forms. Thus, they may be, for example, a solution, a water-free composition, an emulsion or microemulsion of the water-in-oil (W/O) or oil-in-water (O/W) type, a multiple emulsion, for example of the water-in-oil-in-water (W/O/W) type, a gel, a solid stick, an ointment or an aerosol. It is also advantageous to administer ectoines in encapsulated form, for example in collagen matrices and other conventional encapsulation materials, for example as cellulose encapsulations, in gelatine, wax matrices or liposomally encapsulated. In particular, wax matrices, as described in DE-A 43 08 282, have proven favourable. Preference is given to emulsions. OW emulsions are particularly preferred. Emulsions, W/O emulsions and O/W emulsions are obtainable in a conventional manner.

Emulsifiers that can be used are, for example, the known W/O and O/W emulsifiers. It is advantageous to use further conventional co-emulsifiers in the preferred O/W emulsions according to the invention.

Co-emulsifiers which are advantageous according to the invention are, for example, O/W emulsifiers, principally from the group consisting of the substances having HLB values of 11-16, very particularly advantageously having HLB values of 14.5-15.5, so long as the O/W emulsifiers have saturated radicals R and R'. If the O/W emulsifiers have unsaturated radicals R and/or R' or in the case of isoalkyl derivatives, the preferred HLB value of such emulsifiers may also be lower or higher.

It is advantageous to select the fatty alcohol ethoxylates from the group consisting of ethoxylated stearyl alcohols, cetyl alcohols, cetylstearyl alcohols (cetearyl alcohols). Particular preference is given to the following-polyethylene glycol (13) stearyl ether (steareth-13), polyethylene glycol (14) stearyl ether (steareth-14), polyethylene glycol (15) stearyl ether (steareth-15), polyethylene glycol (16) stearyl ether (steareth-16), polyethylene glycol (17) stearyl ether (steareth-17), polyethylene glycol (18) stearyl ether (steareth-18), polyethylene glycol (19) stearyl ether (steareth-19), polyethylene glycol (20) stearyl ether (steareth-20), polyethylene glycol (12) isostearyl ether (isosteareth-12), polyethylene glycol (13) isostearyl ether (isosteareth-13), polyethylene glycol (14) isostearyl ether (isosteareth-14), polyethylene glycol (15) isostearyl ether (isosteareth-15), polyethylene glycol (16) isostearyl ether (isosteareth-16), polyethylene glycol (17) isostearyl ether (isosteareth-17), polyethylene glycol (18) isostearyl ether (isosteareth-18), polyethylene glycol (19) isostearyl ether (isosteareth-19), polyethylene glycol (20) isostearyl ether (isosteareth-20), polyethylene glycol (13) cetyl ether (ceteth-13), polyethylene glycol (14)

cetyl ether (ceteth-14), polyethylene glycol (15) cetyl ether (ceteth-15), polyethylene glycol (16) cetyl ether (ceteth-16), polyethylene glycol (17) cetyl ether (ceteth-17), polyethylene glycol (18) cetyl ether (ceteth-18), polyethylene glycol (19) cetyl ether (ceteth-19), polyethylene glycol (20) cetyl ether (ceteth-20), polyethylene glycol (13) isocetyl ether (isoceteth-13), polyethylene glycol (14) isocetyl ether (isoceteth-14), polyethylene glycol (15) isocetyl ether (isoceteth-15), polyethylene glycol (16) isocetyl ether (isoceteth-16), polyethylene glycol (17) isocetyl ether (isoceteth-17), polyethylene glycol (18) isocetyl ether (isoceteth-18), polyethylene glycol (19) isocetyl ether (isoceteth-19), polyethylene glycol (20) isocetyl ether (isoceteth-20), polyethylene glycol (12) oleyl ether (oleth-12), polyethylene glycol (13) oleyl ether (oleth-13), polyethylene glycol (14) oleyl ether (oleth-14), polyethylene glycol (15) oleyl ether (oleth-15), polyethylene glycol (12) lauryl ether (laureth-12), polyethylene glycol (12) isolauryl ether (isolaureth-12), polyethylene glycol (13) cetylstearyl ether (ceteareth-13), polyethylene glycol (14) cetylstearyl ether (ceteareth-14), polyethylene glycol (15) cetylstearyl ether (ceteareth-15)$_1$ polyethylene glycol (16) cetylstearyl ether (ceteareth-16), polyethylene glycol (17) cetylstearyl ether (ceteareth-17), polyethylene glycol (18) cetylstearyl ether (ceteareth-18), polyethylene glycol (19) cetylstearyl ether (ceteareth-19), polyethylene glycol (20) cetylstearyl ether (ceteareth-20).

It is furthermore advantageous to select the fatty acid ethoxylates from the following group:

polyethylene glycol (20) stearate, polyethylene glycol (21) stearate, polyethylene glycol (22) stearate, polyethylene glycol (23) stearate, polyethylene glycol (24) stearate, polyethylene glycol (25) stearate, polyethylene glycol (12) isostearate, polyethylene glycol (13) isostearate, polyethylene glycol (14) isostearate, polyethylene glycol (15) isostearate, polyethylene glycol (16) isostearate, polyethylene glycol (17) isostearate, polyethylene glycol (18) isostearate, polyethylene glycol (19) isostearate, polyethylene glycol (20) isostearate, polyethylene glycol (21) isostearate, polyethylene glycol (22) isostearate, polyethylene glycol (23) isostearate, polyethylene glycol (24) isostearate, polyethylene glycol (25) isostearate, polyethylene glycol (12) oleate, polyethylene glycol (13) oleate, polyethylene glycol (14) oleate, polyethylene glycol (15) oleate, polyethylene-glycol (16) oleate, polyethylene glycol (17) oleate, polyethylene glycol (18) oleate, polyethylene glycol (19) oleate, polyethylene glycol (20) oleate.

An ethoxylated alkyl ether carboxylic acid or salt thereof which can advantageously be used is sodium laureth-11 carboxylate. An alkyl ether sulfate which can advantageously be used is sodium laureth-14 sulfate. An ethoxylated cholesterol derivative which can advantageously be used is polyethylene glycol (30) cholesteryl ether. Polyethylene glycol (25) soyasterol has also proven successful. Ethoxylated triglycerides which can advantageously be used are the polyethylene glycol (60) evening primrose glycerides.

It is furthermore advantageous to select the polyethylene glycol glycerol fatty acid esters from the group consisting of polyethylene glycol (20) glyceryl laurate, polyethylene glycol (21) glyceryl laurate, polyethylene glycol (22) glyceryl laurate, polyethylene glycol (23) glyceryl laurate, polyethylene glycol (6) glyceryl caprate/caprinate, polyethylene glycol (20) glyceryl oleate, polyethylene glycol (20) glyceryl isostearate, polyethylene glycol (18) glyceryl oleate/cocoate.

It is likewise favourable to select the sorbitan esters from the group consisting of polyethylene glycol (20) sorbitan monolaurate, polyethylene glycol (20) sorbitan monostearate, polyethylene glycol (20) sorbitan monoisostearate, polyethylene glycol (20) sorbitan monopalmitate, polyethylene glycol (20) sorbitan monooleate.

Optional W/O emulsifiers, but ones which may nevertheless be advantageous for the purposes of the invention can be the following:

fatty alcohols having from 8 to 30 carbon atoms, monoglycerol esters of saturated and/or unsaturated, branched and/or unbranched alkane-carboxylic acids having a chain length of from 8 to 24 carbon atoms, in particular 12-18 carbon atoms, diglycerol esters of saturated and/or unsaturated, branched and/or unbranched alkanecarboxylic acids having a chain length of from 8 to 24 carbon atoms, in particular 12-18 carbon atoms, monoglycerol ethers of saturated and/or unsaturated, branched and/or unbranched alcohols having a chain length of from 8 to 24 carbon atoms, in particular 12-18 carbon atoms, diglycerol ethers of saturated and/or unsaturated, branched and/or unbranched alcohols having a chain length of from 8 to 24 carbon atoms, in particular 12-18 carbon atoms, propylene glycol esters of saturated and/or unsaturated, branched and/or unbranched alkanecarboxylic acids having a chain length of from 8 to 24 carbon atoms, in particular 12-18 carbon atoms, and sorbitan esters of saturated and/or unsaturated, branched and/or unbranched alkanecarboxylic acids having a chain length of from 8 to 24 carbon atoms, in particular 12-18 carbon atoms.

Particularly advantageous W/O emulsifiers are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol (2) stearyl ether (steareth-2), glyceryl monolaurate, glyceryl monocaprinate and glyceryl monocaprylate.

Preferred compositions according to the invention are particularly suitable for protecting human skin against ageing processes and against oxidative stress, i.e. against damage by free radicals, as are produced, for example, by sunlight, heat or other influences. In this connection, they are in the various administration forms usually used for this application. For example, they may, in particular, be in the form of a lotion or emulsion, such as in the form of a cream or milk (O/W, W/O, O/W/O, W/O/W), in the form of oily-alcoholic, oily-aqueous or aqueous-alcoholic gels or solutions, in the form of solid sticks or may be formulated as an aerosol.

The composition may comprise cosmetic adjuvants which are usually used in this type of composition, such as, for example, thickeners, softeners, moisturisers, surfactants, emulsifiers, preservatives, antifoams, perfumes, waxes, lanolin, propellants, dyes and/or pigments which colour the composition itself or the skin, and other ingredients usually used in cosmetics.

The dispersant or solubiliser used can be an oil, wax or other fatty substance, a lower monoalcohol or lower polyol or mixtures thereof. Particularly preferred monoalcohols or polyols include ethanol, isopropanol, propylene glycol, glycerol and sorbitol.

A preferred embodiment of the invention is an emulsion in the form of a protective cream or milk which, apart from the compound(s) according to the invention, comprises, for example, fatty alcohols, fatty acids, fatty acid esters, in particular triglycerides of fatty acids, lanolin, natural and synthetic oils or waxes and emulsifiers in the presence of water.

Further preferred embodiments are oily lotions based on natural or synthetic oils and waxes, lanolin, fatty acid esters, in particular triglycerides of fatty acids, or oily-alcoholic lotions based on a lower alcohol, such as ethanol, or a glycerol, such as propylene glycol, and/or a polyol, such as glycerol, and oils, waxes and fatty acid esters, such as triglycerides of fatty acids.

The composition according to the invention may also be in the form of an alcoholic gel which comprises one or more lower alcohols or polyols, such as ethanol, propylene glycol or glycerol, and a thickener, such as siliceous earth. The oily-alcoholic gels also comprise natural or synthetic oil or wax.

The solid sticks consist of natural or synthetic waxes and oils, fatty alcohols, fatty acids, fatty acid esters, lanolin and other fatty substances.

If a composition is formulated as an aerosol, the customary propellants, such as alkanes, fluoroalkanes and chlorofluoroalkanes, are generally used.

The cosmetic composition may also be used to protect the hair against photochemical damage in order to prevent changes of colour shade, bleaching or damage of a mechanical nature. In this case, a suitable formulation is in the form of a rinse-out shampoo, lotion, gel or emulsion, the composition in question being applied before or after shampooing, before or after colouring or bleaching or before or after permanent waving. It is also possible to select a composition in the form of a lotion or gel for styling or treating the hair, in the form of a lotion or gel for brushing or blowwaving, in the form of a hair lacquer, permanent waving composition, colorant or bleach for the hair. Besides the compound(s) of the formula I, the composition having light-protection properties may comprise various adjuvants used in this type of composition, such as surfactants, thickeners, polymers, softeners, preservatives, foam stabilisers, electrolytes, organic solvents, silicone derivatives, oils, waxes, antigrease agents, dyes and/or pigments which colour the composition itself or the hair, or other ingredients usually used for hair care.

The present invention furthermore relates to a process for the preparation of a composition which is characterised in that at least one compound of the formula I containing radicals as described above is mixed with a cosmetically or dermatologically or food-suitable carrier, and to the use of a compound of the formula I for the preparation of a composition.

The compositions according to the invention can be prepared here with the aid of techniques which are well known to the person skilled in the art.

The mixing can result in dissolution, emulsification or dispersal of the compound of the formula I in the carrier.

In a process preferred in accordance with the invention, the compound of the formula I is prepared by cyclisation of a correspondingly substituted o-hydroxyacetophenone using an anhydride or using an acyl chloride under basic conditions. The acyl protecting groups can subsequently be removed. The reaction here can be carried out analogously to Kelly, T; Kim M. H.; *J. Org. Chem.* 1992, 57, 1593-97. Alternatively, the free hydroxyl groups are acylated, followed by a Baker-Venkatamaran rearrangement under basic conditions with subsequent ring closure under acidic conditions. Corresponding reactions, adaptation of which to the compounds desired here presents absolutely no problems to the person skilled in the art, are disclosed in the patent application WO 2002/060889.

Conventional reactions on the ring system or derivatisation of the functional groups enable further derivatives of the formula I to be obtained. The reaction condition necessary for such reactions, such as, for example, oxidations, reductions, transesterifications, etherifications, can easily be found by a person skilled in the art for syntheses of this type in the generally available literature on organic reactions.

It has also been noted that compounds of the formula I can have a stabiuising effect on the composition. When used in corresponding products, the latter are thus also stable for longer and do not change their appearance. In particular, the effectiveness of the ingredients, for example vitamins, is retained even in the case of application over extended periods or extended storage. This is, inter alia, particularly advantageous in the case of compositions for protecting the skin against the effect of UV rays since these cosmetics are exposed to particularly high stresses by UV radiation.

The positive effects of compounds of the formula I give rise to their particular suitability for use in cosmetic or pharmaceutical compositions.

The properties of compounds of the formula I should likewise be regarded as positive for use in foods or as food supplements or as functional foods. The further explanations given for foods also apply correspondingly to food supplements and functional foods.

The foods which can be enriched with one or more compounds of the formula I in accordance with the present invention include all materials which are suitable for consumption by animals or consumption by humans, for example vitamins and provitamins thereof, fats, minerals or amino acids. (The foods may be solid, but also liquid, i.e. in the form of a beverage). The present invention accordingly furthermore relates to the use of a compound of the formula I as food additive for human or animal nutrition, and to compositions which are foods or food supplements and comprise corresponding excipients.

Foods which can be enriched with one or more compounds of the formula I in accordance with the present invention are, for example, also foods which originate from a single natural source, such as, for example, sugar, unsweetened juice, squash or puree of a single plant species, such as, for example, unsweetened apple juice (for example also a mixture of different types of apple juice), grapefruit juice, orange juice, apple compote, apricot squash, tomato juice, tomato sauce, tomato puree, etc. Further examples of foods which can be enriched with one or more compounds of the formula I in accordance with the present invention are corn or cereals from a single plant species and materials produced from plant species of this type, such as, for example, cereal syrup, rye flour, wheat flour or oat bran. Mixtures of foods of this type are also suitable for being enriched with one or more compounds of the formula I in accordance with the present invention, for example multivitamin preparations, mineral mixtures or sweetened juice. As further examples of foods which can be enriched with one or more compounds of the formula I in accordance with the present invention, mention may be made of food compositions, for example prepared cereals, biscuits, mixed drinks, foods prepared especially for children, such as yogurt, diet foods, low-calorie foods or animal feeds.

The foods which can be enriched with one or more compounds of the formula I in accordance with the present invention thus include all edible combinations of carbohydrates, lipids, proteins, inorganic elements, trace elements, vitamins, water or active metabolites of plants and animals.

The foods which can be enriched with one or more compounds of the formula I in accordance with the present invention are preferably administered orally, for example in the form of meals, pills, tablets, capsules, powders, syrup, solutions or suspensions.

The foods according to the invention enriched with one or more compounds of the formula I can be prepared with the aid of techniques which are well known to the person skilled in the art.

Due to their action, compounds of the formula I are also suitable as medicament ingredients, Compounds of the formula I can be used, for example, for preventative treatment of inflammation and allergies of the skin and in certain cases for preventing certain types of cancer. Compounds of the formula I are particularly suitable for the preparation of a medicament for the treatment of inflammation, allergies and irritation, in particular of the skin. It is furthermore possible to prepare medicaments which act as a vein tonic, as cuperose inhibitor, as chemical, physical or actinic erythema inhibitor, as agent for the treatment of sensitive skin, as decongestant, as desiccant, as slimming agent, as anti-wrinkle agent, as stimulator for the synthesis of components of the extracellular matrix, as strengthening agent for improving skin elasticity, and as anti-ageing agent. Furthermore, compounds of the formula I which are preferred in this connection exhibit antiallergic and antiinflammatory and antiirritative actions. They are therefore suitable for the preparation of medicaments for the treatment of inflammation or allergic reactions.

The invention is explained in greater detail below by means of examples. The invention can be carried out throughout the range claimed and is not restricted to the examples given here.

EXAMPLES

Example 1

Preparation of 2-ethoxycarbonyl-7-hydroxychromone

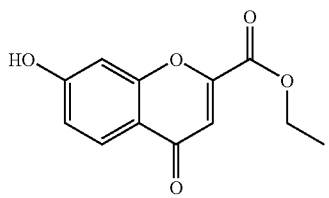 [SMILES: CCOC(=O)c1cc(=O)c2ccc(O)cc2o1]

Sodium (7.6 g, 330 mmol) is initially introduced under an Ar atmosphere, and ethanol (500 ml) is slowly added dropwise. The mixture is stirred for approximately a further 1 hour until the sodium has completely dissolved and is subsequently cooled to RT using an ice bath. 2',4'-Dihydroxyacetophenone (10 g, 66 mmol) and diethyl oxalate (36 ml, 266 mmol) dissolved in 60 ml of EtOH (brown-orange clear solution) are added dropwise. The solution is stirred at 70° C. for 2 hours. The clear solution is cooled to 0° C. using an ice/water bath and adjusted from pH 13 to pH 4 using about 50 ml of HCl (c=32%). Some of the ethanol is then removed from the suspension under reduced pressure. The remaining suspension is added to 300 ml of ice-water and extracted with $CH_2Cl_2$, the aqueous phase is extracted by shaking 2× with $CH_2Cl_2$, the org. phases are combined, extracted 3× with deionised water and 1× with saturated NaCl solution, and the org. phase is dried using Na sulfate, filtered and evaporated to dryness. Yield: 29.1 g of red-brown slurry-like solid.

100 ml of acetic acid and 1 ml of conc. sulfuric acid are added to the crude product, and the mixture is refluxed for 2 hours with stirring and cooled, and the solid which precipitates in the process is filtered off via a suction filter, washed with a little $CH_3COOH$ and subsequently with deionised water until neutral and dried overnight in a vacuum drying cabinet at 40° C. and 200 mbar.

Yield: 10.1 g=65.6% of theory of pale-pink pulverulent solid,

Recrystallisation is carried out from a mixture of toluene and methanol.

Yield: 6.6 g=42.9% of theory of beige, fine crystals (HPLC=100%).

$^1$H NMR (300 MHz) in DMSO δ (ppm): 1.35 (t, 3H), 4.37 (q, 2H), 6.84 (s, 1H), 6.9 (d, 1H), 6.96 (dd, 1H), 7.9 (d, 1H), 11.0 (bs, 1O$\underline{H}$).

MS (m/e): 234 (M$^+$)

Example 2

Preparation of 7-hydroxy-4-oxo-4H-chromone-2-carboxylic acid

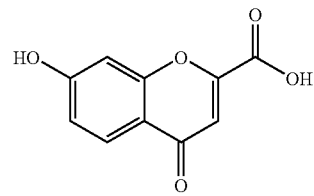 [SMILES: O=C(O)c1cc(=O)c2ccc(O)cc2o1]

2-Ethoxycarbonyl-7-hydroxychromone (14.5 g, 62 mmol) is initially introduced dissolved in ethanol (400 ml) at 50° C., and sodium carbonate (20 g, 190 mmol) dissolved in deionised $H_2O$ (200 ml) is added dropwise. The mixture is refluxed at 80° C. for 3 hours with stirring. After cooling, the mixture is acidified using 2N HCl. The precipitated white solid is filtered off with suction, washed until neutral and dried.

Yield: 6.5 g=50.9% of theory of a virtually white powder;

$^1$H NMR (300 MHz) in DMSO δ (ppm): 6.8 (s, 1H), 6.9 (d, 1H), 6.95 (dd, 1H), 7.9 (d, 1H), 11.0 (bs, 1O$\underline{H}$), 14.5 (bs, 1COO$\underline{H}$)

MS (m/e): 206 (M$^+$)

Example 2a

Preparation of 1-ethylhexyl 7-hydroxy-4-oxo-4H-chromone-2-carboxylate

The ester is obtained by esterification of the acid from Example 2 using 1-ethylhexyl alcohol.

$^1$H NMR (300 MHz) in CDCl$_3$ δ (ppm): 0.79-0.88 (m, 6H), 1.18-1.37 (m, 8H), 1.65 (ddd, 1H), 7.02-7.06 (m, 1H+2H arom.), 8.02 (d, 1H arom.)

Example 3

Preparation of 2-methoxy-7-hydroxy-4H-chromen-4-one

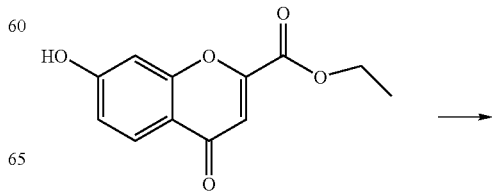

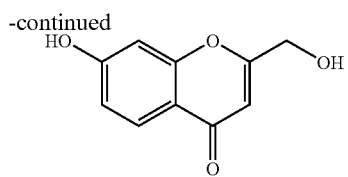

Ethyl 7-hydroxychromen-4-one-2-carboxylate (2 g, 8.538 mmol) and granulated and dried calcium chloride (1 g, 9.01 mmol) are initially introduced, and ethanol (absolute, 40 ml) is added. Sodium borohydride (1.33 g, 35.157 mmol) is subsequently added in portions with ice cooling. The reaction mixture is stirred at RT for 2 hours, then again cooled using an ice bath, and sodium borohydride (0.45 g, 11.895 mmol) is again added. The mixture is stirred overnight at RT.

The ethanol is subsequently removed in a rotary evaporator (bath temperature: 50° C.), 60 ml of deionised water are carefully added to the residue, and the suspension is acidified dropwise using 2N HCl. About 100 g of ice are subsequently added to the solution, and the mixture is stirred for half an hour, during which a white solid precipitates, which is filtered off with suction and dried at 45° C. in a vacuum drying cabinet. 1.1 g of white solid. Yield. 67%

$^1$H NMR in DMSO δ (ppm): 4.4 (s, 2H), 6.2 (s, 1H), 6.8 (d, 1H), 6.9 (dd, 1H), 7.9 (d, 1H).

MS (m/e): 192 (M$^+$);

Example 4

Preparation of 5,7-dihydroxy-4-oxo-4H-chromene-2-carboxylic acid

Step 1:

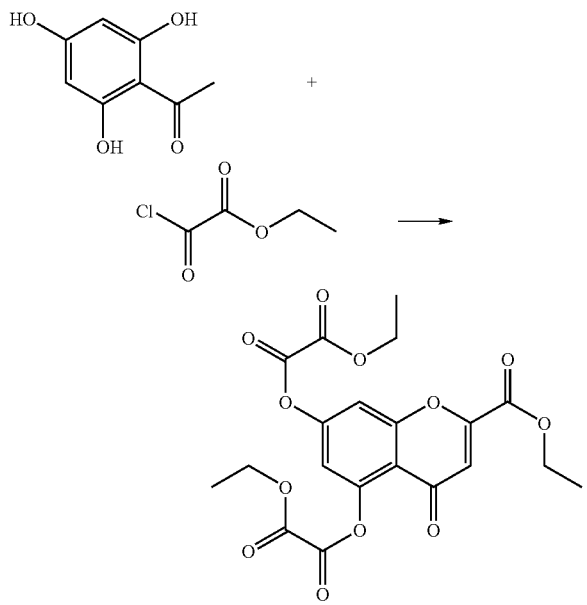

2,4,6-Trihydroxyacetophenone dissolved in pyridine is initially introduced under an argon atmosphere, and a little 4-(dimethylamino)pyridine (catalytic amount) is introduced. The ethyl chloroformylformate is then slowly added dropwise. When everything has been added, the apparatus is heated to 80° C. using an oil bath and stirred at this temperature for 2 hours.

The apparatus is allowed to cool to room temperature, the dark-brown suspension is added to about 200 ml of ice-water, 200 ml of CH$_2$Cl$_2$ are added, and the mixture is extracted. The aqueous phase is extracted by shaking a further 2× with 50 ml of CH$_2$Cl$_2$, and the black org. phases are combined and washed 2× with 50 ml of deionised water, 3× with 2 molar HCl (pyridine-free) and 1× with saturated NaCl solution, leaving a clear black-brown org. phase, which is dried using Na$_2$SO$_4$. The organic phase is passed through a glass frit with a little silica gel #7734 slurried in CH$_2$Cl$_2$/EEE (5:1), the filter cake is rinsed with about 250 ml of CH$_2$Cl$_2$/EEE (5:1), and the solution is evaporated in a rotary evaporator. Yield: 8.5 g of yellow solid. This solid is used as it is for the next step.

Step 2:

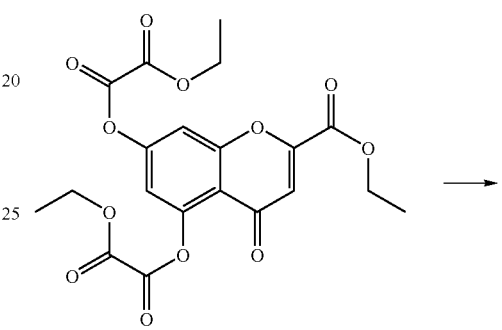

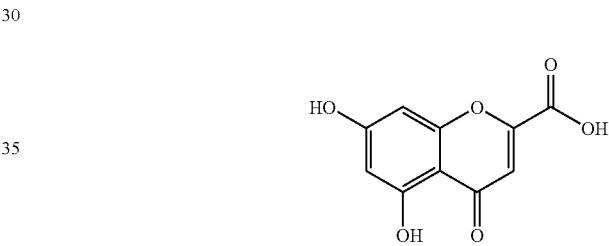

2-Ethoxycarbonyl-7-ethoxyoxalyloxy-4-oxo-4H-chromen-5-yl ethyl oxalate from Step 1 dissolved in ethanol is initially introduced at room temperature, and Na$_2$CO$_3$ dissolved in deionised H$_2$O is added dropwise. The mixture is subsequently heated to 70° C. and stirred at this temperature for a further 4 hours. After cooling, 100 ml of ethyl acetate are added to the reaction mixture, which is slightly acidified using 1N HCl. The aqueous phase is separated off and extracted. The org. phases are combined, washed 3× with deionised H$_2$O and 1× with sat. NaCl solution, dried using Na$_2$SO$_4$, filtered and evaporated in a rotary evaporator. Recrystallisation gives 0.4 g of yellow fine crystals (HPLC=98.4%).

$^1$H NMR (300 MHz) in DMSO δ (ppm): 6.2 (d, 1H), 6.4 (d, 1H), 6.8 (s, 1H), 11.1 (bs, 1H), 12.5 (bs, 1H).

MS (m/e): 222 (M$^+$)

Example 4a

Preparation of 1-ethylhexyl 5,7-dihydroxy-4-oxo-4H-chromene-2-carboxylate

The ester is obtained by esterification of the acid from Example 4 using 1-ethylhexyl alcohol.

Example 5

Preparation of 5,7-diacetoxy-3-acetyl-2-methylchromen-4-one

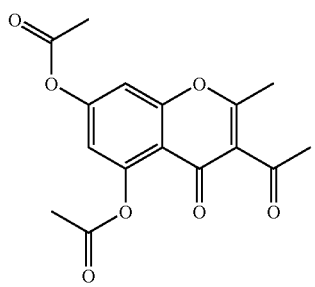 [SMILES: CC(=O)Oc1cc(OC(C)=O)c2c(=O)c(C(C)=O)c(C)oc2c1]

2,4,6-Trihydroxyacetophenone dissolved in acetic anhydride is initially introduced, and sodium acetate is added. The suspension is refluxed with stirring for 10 hours. The reaction mixture is subsequently poured into about 300 ml of ice-water and extracted 2× with ethyl acetate (EA), and the org. phases are combined and washed 3× with deionised $H_2O$. The solution which remains is washed further with $Na_2HCO_3$ solution. The organic phase is dried over $Na_2SO_4$, filtered and evaporated in a rotary evaporator.

$^1$H NMR (300 MHz) in DMSO δ (ppm): 7.1 (d, 1H), 7.4 (d, 1H)

MS (m/e): 318 (M$^+$)

Example 6

Preparation of 5,7-dihydroxy-2-methylchromen-4-one

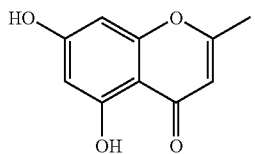

5,7-Diacetoxy-3-acetyl-2-methylchromen-4-one is refluxed for 1 hour with 40 ml of 10% sodium carbonate solution. After cooling, the suspension is adjusted to a pH of about 6 using 2N HCl and cooled. The precipitate is filtered off, giving 0.6 g of very pale brown powder ($T_M$=279.9° C.)

$^1$H NMR (300 MHz) in DMSO δ (ppm). 2.3 (s, 3H), 6.15 (s, 1H), 6.18 (d, 1H), 6.3 (d, 1H), 10.8 (bs, 1OH), 12.8 (s, 1OH)

MS (m/e): 192 (M$^+$)

Example 7

Preparation of 5,7-dihydroxy-2-ethylpentylchromen-4-one

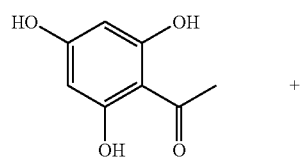 +

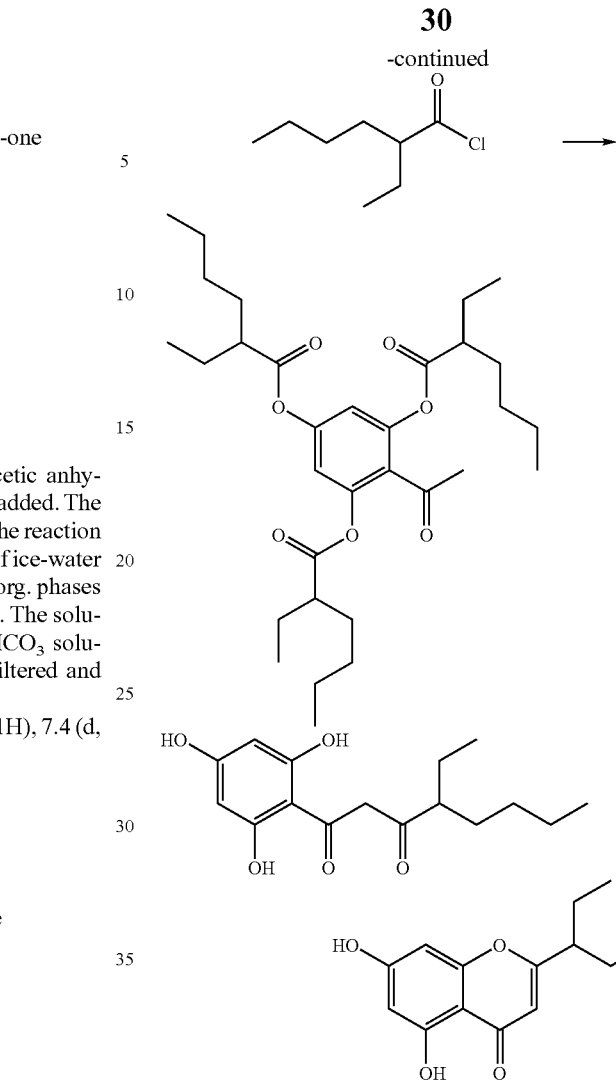

1st Step:

2,4,6-Trihydroxyacetophenone (5 g, 26.3 mmol) is added to 90 ml of toluene, and 14 g of potassium carbonate dissolved in 70 ml of deionised water and 1 g of tetra-n-butylammonium hydrogensulfate are added to the solution. 2-Ethylhexanoyl chloride (20.5 ml, 119.7 mmol) is added dropwise to the two-phase mixture over the course of 10 minutes with vigorous stirring. The two-phase mixture is subsequently heated at 70° C. for 5 hours with stirring.

The upper dark-red organic phase is subsequently separated off, the aqueous phase is extracted by shaking twice with dichloromethane, and the organic phases are combined, washed with saturated sodium chloride solution, dried over sodium sulfate, filtered and evaporated to dryness in a Rotavapor (bath temperature: 50° C.).

M(R): 19.3 g

2nd Step 19.3 g of the product from the 1st step are dissolved in 600 ml of THF, and lithium hydroxide (4.4 g, 183.7 mmol) is added. The mixture is subsequently refluxed for 5.5 hours. The red-brown reaction solution is poured onto about 800 g of ice+100 ml of conc. HCl and extracted a number of times with dichloromethane, and the orange combined organic phases are washed with saturated sodium chloride solution, dried over sodium sulfate, filtered and evaporated to dryness in a rotary evaporator (bath temperature: 50° C.).

M(R): 17.2 g

3rd Step:

17.2 g of the product from the 2nd step are dissolved in 200 ml of acetic acid, and 2 ml of conc. sulfuric acid are added. The mixture is subsequently refluxed for 7 hours with stirring. The red-brown cloudy solution is poured onto about 500 g of ice, the red-brown precipitated solid is filtered off via a suction filter, taken up in dichloromethane and, together with the aqueous filtrate, extracted a number of times by shaking with dichloromethane, and the combined organic phases are washed with saturated sodium chloride solution, dried over sodium sulfate, filtered and evaporated to dryness in a rotary evaporator (bath temperature: 50° C.).

m(R): 18.4 g of residue TLC: one spot

The residue is dissolved in a little methanol, and deionised water is added, whereupon a beige solid precipitates, which is filtered off via a small suction filter.

m(K): 1.65 g of beige solid

The filtrate is evaporated again, and 100 ml of heptane are added to the distillation residue, whereupon a solid precipitates, which is filtered off via a suction filter.

m(K2); 2.27 g of pale-brown solid m(K tot.): 3.92 g are 52.3% of the theoretical yield, based on the amount of 2,4,6-trihydroxyacetophenone used.

$^1$H NMR (300 MHz) in DMSO δ (ppm): 0.9 (m, 6H), 1.15-1.3 (m, 4H), 1.55-1.65 (m, 4H), 2.45 (q, 1H), 6.17 (s, 1H), 6.2 (d, 1H), 6.35 (d 1H), 10.75 (bs, O$\underline{H}$), 12.85 (s, O$\underline{H}$).

MS (m/e): 276 (M$^+$)

The following is prepared analogously: 5,7-dihydroxy-3-(2-methoxyacetyl)-2-methoxymethylchromen-4-one

Example 8

Preparation of 7-isopropyl-4-oxo-4H-chromone-3-carbaldehyde

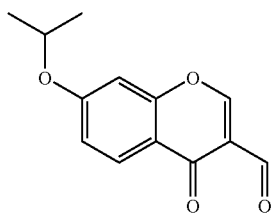 [SMILES: CC(C)Oc1ccc2c(=O)c(C=O)coc2c1]

7-Hydroxy-4-oxo-4H-chromone-3-carbaldehyde (2 g, 10.5 mmol) is dissolved in N,N-dimethylformamide (25 ml) under an N$_2$ atmosphere, potassium carbonate (1.8 g, 13 mmol) and potassium iodide (50 mg) are added, and the mixture is stirred at RT for 1 hour. 2-Bromopropane (2 ml, 21 mmol) is then slowly added dropwise, and the mixture is heated at 55° C. for 2 hours. A further 2 ml of 2-bromopropane are added, and the mixture is stirred at 55° C. for a further 2.5 hours. After stirring at RT for 12 hours, the reaction mixture is introduced into 60 ml of deionised water, acidified using dilute HCl and extracted with 150 ml of EA. The aqueous phase is extracted a further 2× with EA. The combined org. phases are extracted by shaking 2× with 150 ml of deionised water and 1× with saturated NaCl solution, dried using Na sulfate and filtered, and the solvent is stripped off. For purification, the crude product is dissolved in 10 ml of eluent (CH$_2$Cl$_2$/MeOH 9.5/0.5) and filtered through 250 g of silica gel #109385. Yield: 281 mg=11.52% of theory. (HPLC content: 89.3%).

$^1$H NMR (300 MHz) in DMSO 3 (ppm): 1.3 (d, 6H), 4.9 (m, 1H), 7.1 (dd, 1H), 7.3 (d, 1H), 8.85 (s, 1H), 10.1 (s, 1H).

Example 9

Preparation of L-ascorbyl 6-[5,7-dihydroxy-4-oxo-4H-chromone-2-carboxylate]

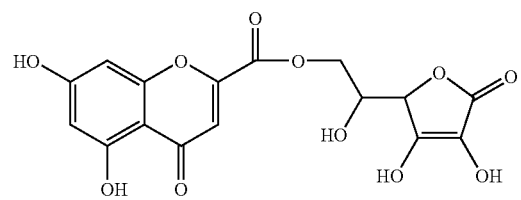 [SMILES: O=C1OC(C(O)COC(=O)c2cc(=O)c3c(O)cc(O)cc3o2)C(O)=C1O]

5,7-Dihydroxy-4-oxo-4H-chromone-2-carboxylic acid (400 mg, 1.8 mmol) dissolved in 95-97% sulfuric acid (10 ml) is initially introduced under an argon atmosphere and warmed to 55° C. Ten 100 mg portions of L-(+)-ascorbic acid are introduced slowly, during which the temperature is held at a maximum of 75° C. The mixture is subsequently stirred at this temperature for 12 hours.

The reaction mixture is cooled using an ice bath and introduced into 50 ml of ice-water, EA is added, the mixture is filtered through Celite, the aqueous phase is separated off and extracted again with a little EA, and the org. phases are combined, washed 4× with about 20 ml of deionised H$_2$O each time and 1× with sat. NaCl solution until neutral, dried using Na$_2$SO$_4$, filtered and evaporated in a rotary evaporator.

Yield: 250 mg

HPLC-ESI-MS shows [M+H]$^+$=365.1

Example 10

Investigations of Efficacy

Example 10a

Antiinflammatory Properties (PGE2 Assay)

Human keratinocytes of the cell line NCTC R13 are pre-cultivated for 24 hours at 37° C. in a 5% CO$_2$ atmosphere with DMEM culture medium (Life Technologies). The cells are treated with LU for 24 hours, and the culture medium is then removed. A fresh culture medium containing the inflammation-triggering active ingredient phorbol myristate acetate (PMA; 0.1 g/ml) and LU is added. After incubation for 24 hours, the culture medium is collected and analysed. By means of an ELISA DE0100 kit (R&D Systems), the release is used in order to investigate the release of the inflammation marker prostaglandin E2 (PGE2) (Table).

TABLE

| PGE2 release from human keratinocytes | | | | | |
|---|---|---|---|---|---|
| | 0.2 mM LU | 0.04 mM LU | 0.008 mM LU | Control (only PMA) | Neg. control (no PMA) |
| PGE2 (ng/ml) | 6.31 | 226.39 | 340.62 | 302.02 | 0.018 |
| Number of tests | 3 | 3 | 3 | 3 | 3 |

TABLE-continued

PGE2 release from human keratinocytes

|  | 0.2 mM LU | 0.04 mM LU | 0.008 mM LU | Control (only PMA) | Neg. control (no PMA) |
|---|---|---|---|---|---|
| Standard deviation | 0.5 | 11.92 | 17.93 | 9.31 | 0.001 |
| % compared with control | 2 | 75 | 113 | 100 | 0 |

5,7-Dihydroxy-2-methylchromen-4-one in doses of 0.2 mM and 0.04 mM exhibits a clear reduction in PGE2 release on exposure to PMA.

Example 10b

Action on the Activity of Leukocyte Elastase 5,7-Dihydroxy-2-methylchromen-4-one in TRIS buffer (500 mM) is incubated for 10 minutes on ice with elastase (from human leukocytes; Sigma E8140; 100 mU/well). 5 μg/well of elastin are subsequently added, and the plates are incubated at 37° C. for 2 hours. The fluorescence is determined using a Spectromax Gemini spectrometer (Molecular Devices) at λex=485 nm and λem=538 nm.

TABLE

Leukocyte elastase activity

|  | 200 μM LU | 40 μM LU | Control (0.1 mM AAPV) | Neg. control |
|---|---|---|---|---|
| Fluorescence intensity | 1096.4 | 2195.9 | 96.0 | 2430.2 |
| Number of tests | 3 | 3 | 3 | 3 |
| Standard deviation | 53 | 33 | 7 | 62 |
| % compared with control | 45 | 90 | 4 | 100 |
| % quenching | 19 | 0 | 0 | — |
| Inhibition (%) | 45 | 10 | 96 | — |

5,7-Dihydroxy-2-methylchromen-4-one in doses of 200 μM and 40 μM exhibits clear inhibition of the elastase activity.

Example 10c

Action on the Activity of Hyaluronidase 5,7-Dihydroxy-2-methylchromen-4-one in phosphate buffer (0.1 M) is pre-incubated with hyaluronidase (HYAL, Sigma type IV-S, H3884; 1 mg/l in phosphate buffer (0.1 M)). Hyaluronic acid (HA, Sigma H-1876; 1.2 mg/ml) is subsequently added, and the mixture is incubated at 37° C. for 1 hour. The remaining hyaluronic acid (HA) is subsequently precipitated using serum albumen (BSA, Sigma A7888) and determined photometrically.

TABLE

Hyaluronidase activity

|  | 25 mM LU | 12.5 mM LU | 6.25 mM LU | 3.125 mM LU | Control (only HA, no enzyme) | Control (no LU) |
|---|---|---|---|---|---|---|
| Hyaluronidase activity | 37 | 63 | 81 | 91 | 0 | 100 |
| Hyaluronidase inhibition | 63 | 37 | 19 | 9 | — | 0 |

5,7-Dihydroxy-2-methylchromen-4-one in the doses investigated exhibits clear inhibition of hyaluronidase activity. 50% inhibition ($IC_{50}$) is achieved at about 20 mM of 5,7-dihydroxy-2-methylchromen-4-one.

Example 11

Compositions

Formulations for cosmetic compositions comprising compounds according to Examples 1-3 are shown by way of example below. The INCI names of the commercially available compounds are also shown.

UV-Pearl, OMC stands for the composition having the INCI name: Water (for EU: Aqua), Ethylhexyl Methoxycinnamate, Silica, PVP, Chlorphenesin, BHT; this composition is commercially available under the name Eusolex®UV Pearl™ OMC from Merck KGaA, Darmstadt.

The other UV Pearl products indicated in the tables are each of analogous composition with OMC replaced by the UV filter indicated.

TABLE 1

W/O emulsions (data in % by weight)

|  | 1-1 | 1-2 | 1-3 | 1-4 | 1-5 | 1-6 | 1-7 | 1-8 | 1-9 | 1-10 |
|---|---|---|---|---|---|---|---|---|---|---|
| Titanium Dioxide |  | 2 | 5 |  |  |  |  |  |  | 3 |
| 2-Methyl-5,7-dihydroxy-chromen-4-one | 5 | 3 | 2 | 1 | 2 |  |  |  | 1 | 1 |
| 2-(1-Ethylhexyl)-5,7-dihydroxychromen-4-one |  |  |  |  |  | 1 | 2 | 1 |  |  |
| Zinc Oxide |  |  |  |  |  |  |  | 5 | 2 |  |
| UV-Pearl, OMC | 30 | 15 | 15 | 15 | 15 | 15 | 15 | 15 | 15 | 15 |
| Polyglyceryl-3-Dimerate | 3 | 3 | 3 | 3 | 3 | 3 | 3 | 3 | 3 | 3 |
| Cera Alba | 0.3 | 0.3 | 0.3 | 0.3 | 0.3 | 0.3 | 0.3 | 0.3 | 0.3 | 0.3 |
| Hydrogenated Castor Oil | 0.2 | 0.2 | 0.2 | 0.2 | 0.2 | 0.2 | 0.2 | 0.2 | 0.2 | 0.2 |
| Paraffinium Liquidum | 7 | 7 | 7 | 7 | 7 | 7 | 7 | 7 | 7 | 7 |
| Caprylic/Capric Triglyceride | 7 | 7 | 7 | 7 | 7 | 7 | 7 | 7 | 7 | 7 |
| Hexyl Laurate | 4 | 4 | 4 | 4 | 4 | 4 | 4 | 4 | 4 | 4 |
| PVP/Eicosene Copolymer | 2 | 2 | 2 | 2 | 2 | 2 | 2 | 2 | 2 | 2 |
| Propylene Glycol | 4 | 4 | 4 | 4 | 4 | 4 | 4 | 4 | 4 | 4 |
| Magnesium Sulfate | 0.6 | 0.6 | 0.6 | 0.6 | 0.6 | 0.6 | 0.6 | 0.6 | 0.6 | 0.6 |
| Tocopherol | 0.5 | 0.5 | 0.5 | 0.5 | 0.5 | 0.5 | 0.5 | 0.5 | 0.5 | 0.5 |

TABLE 1-continued

W/O emulsions (data in % by weight)

| | | | | | | | | | | |
|---|---|---|---|---|---|---|---|---|---|---|
| Tocopheryl Acetate | 0.5 | 0.5 | 0.5 | 0.5 | 0.5 | 0.5 | 0.5 | 0.5 | 0.5 | 0.5 |
| Cyclomethicone | 0.5 | 0.5 | 0.5 | 0.5 | 0.5 | 0.5 | 0.5 | 0.5 | 0.5 | 0.5 |
| Propylparaben | 0.05 | 0.05 | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 | 0.15 | 0.15 |
| Water | to 100 | to 100 | to 100 | to 100 | to 100 | to 100 | to 100 | to 100 | to 100 | to 100 |

| | 1-11 | 1-12 | 1-13 | 1-14 | 1-15 | 1-16 | 1-17 | 1-18 |
|---|---|---|---|---|---|---|---|---|
| Titanium Dioxide | 3 | | 2 | | 3 | | 2 | 5 |
| Benzylidene Malonate Polysiloxane | | 1 | 0.5 | | | | | |
| Methylene Bis-benzotriazolyl Tetramethylbutylphenol | 1 | 1 | 0.5 | | | | | |
| 2-(1-Ethylhexyl)-5,7-dihydroxy-chromen-4-one | 5 | 3 | 2 | 5 | 1 | 3 | 7 | 2 |
| Polyglyceryl-3-Dimerate | 3 | 3 | 3 | 3 | | | | |
| Cera Alba | 0.3 | 0.3 | 0.3 | 0.3 | 2 | 2 | 2 | 2 |
| Hydrogenated Castor Oil | 0.2 | 0.2 | 0.2 | 0.2 | | | | |
| Paraffinium Liquidum | 7 | 7 | 7 | 7 | | | | |
| Caprylic/Capric Triglyceride | 7 | 7 | 7 | 7 | | | | |
| Hexyl Laurate | 4 | 4 | 4 | 4 | | | | |
| PVP/Eicosene Copolymer | 2 | 2 | 2 | 2 | | | | |
| Propylene Glycol | 4 | 4 | 4 | 4 | | | | |
| Magnesium Sulfate | 0.6 | 0.6 | 0.6 | 0.6 | | | | |
| Tocopherol | 0.5 | 0.5 | 0.5 | 0.5 | | | | |
| Tocopheryl Acetate | 0.5 | 0.5 | 0.5 | 0.5 | 1 | 1 | 1 | 1 |
| Cyclomethicone | 0.5 | 0.5 | 0.5 | 0.5 | | | | |
| Propylparaben | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 |
| Dicocoyl Pentyerythrityl Citrate (and) Sorbitan Sesquioleate (and) Cera Alba (and) Aluminium Stearate | | | | | 6 | 6 | 6 | 6 |
| PEG-7 Hydrogenated Castor Oil | | | | | 1 | 1 | 1 | 1 |
| Zinc Stearate | | | | | 2 | 2 | 2 | 2 |
| Oleyl Erucate | | | | | 6 | 6 | 6 | 6 |
| Decyl Oleate | | | | | 6 | 6 | 6 | 6 |
| Dimethicone | | | | | 5 | 5 | 5 | 5 |
| Tromethamine | | | | | 1 | 1 | 1 | 1 |
| Glycerine | | | | | 5 | 5 | 5 | 5 |
| Allantoin | | | | | 0.2 | 0.2 | 0.2 | 0.2 |
| Water | | to 100 | to 100 | to 100 | to 100 | to 100 | to 100 | to 100 |

| | 1-19 | 1-20 | 1-21 | 1-22 | 1-23 | 1-24 | 1-25 | 1-26 | 1-27 | 1-28 | 1-29 |
|---|---|---|---|---|---|---|---|---|---|---|---|
| Titanium Dioxide | | 2 | 5 | | | | | | | 3 | 3 |
| Benzylidene Malonate Polysiloxane | | | | 1 | | | | | 1 | 1 | |
| Zinc Oxide | | | | | | | | 5 | 2 | | |
| 2-Methyl-5,7-dihydroxychromen-4-one | 5 | 5 | 5 | 5 | 7 | 5 | 5 | 5 | 5 | 5 | 8 |
| UV-Pearl, OCR | | 10 | | | | | | | | | 5 |
| UV-Pearl, EthylhexylDimethylPABA | | | 10 | | | | | | | | |
| UV-Pearl, Homosalate | | | | 10 | | | | | | | |
| UV-Pearl, Ethylhexyl Salicylate | | | | | 10 | | | | | | |
| UV-Pearl, OMC. BP-3 | | | | | | 10 | | | | | |
| UV-Pearl, OCR. BP-3 | | | | | | | 10 | | | | |
| UV-Pearl, Ethylhexyl Dimethyl PABA, BP-3 | | | | | | | | 10 | | | |
| UV-Pearl, Homosalate, BP-3 | | | | | | | | | 10 | | |
| UV-Pearl, Ethylhexyl Salicylate, BP-3 | | | | | | | | | | 10 | |
| BMDBM | | | | | | | | | | | 2 |
| UV-Pearl, OMC, 4-Methylbenzylidene Camphor | 25 | | | | | | | | | | |
| Polyglyceryl-3-Dimerate | 3 | 3 | 3 | 3 | 3 | 3 | 3 | 3 | 3 | 3 | 3 |
| Cera Alba | 0.3 | 0.3 | 0.3 | 0.3 | 0.3 | 0.3 | 0.3 | 0.3 | 0.3 | 0.3 | 0.3 |
| Hydrogenated Castor Oil | 0.2 | 0.2 | 0.2 | 0.2 | 0.2 | 0.2 | 0.2 | 0.2 | 0.2 | 0.2 | 0.2 |
| Paraffinium Liquidum | 7 | 7 | 7 | 7 | 7 | 7 | 7 | 7 | 7 | 7 | 7 |
| Caprylic/Capric Triglyceride | 7 | 7 | 7 | 7 | 7 | 7 | 7 | 7 | 7 | 7 | 7 |
| Hexyl Laurate | 4 | 4 | 4 | 4 | 4 | 4 | 4 | 4 | 4 | 4 | 4 |
| PVP/Eicosene Copolymer | 2 | 2 | 2 | 2 | 2 | 2 | 2 | 2 | 2 | 2 | 2 |
| Propylene Glycol | 4 | 4 | 4 | 4 | 4 | 4 | 4 | 4 | 4 | 4 | 4 |

TABLE 1-continued

| W/O emulsions (data in % by weight) | | | | | | | | | | | |
|---|---|---|---|---|---|---|---|---|---|---|---|
| Magnesium Sulfate | 0.6 | 0.6 | 0.6 | 0.6 | 0.6 | 0.6 | 0.6 | 0.6 | 0.6 | 0.6 | 0.6 |
| Tocopherol | 0.5 | 0.5 | 0.5 | 0.5 | 0.5 | 0.5 | 0.5 | 0.5 | 0.5 | 0.5 | 0.5 |
| Tocopheryl Acetate | 0.5 | 0.5 | 0.5 | 0.5 | 0.5 | 0.5 | 0.5 | 0.5 | 0.5 | 0.5 | 0.5 |
| Cyclomethicone | 0.5 | 0.5 | 0.5 | 0.5 | 0.5 | 0.5 | 0.5 | 0.5 | 0.5 | 0.5 | 0.5 |
| Propylparaben | 0.05 | 0.05 | 0.05 | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 | 0.15 | 0.15 | 0.15 |
| Water | | | | | | to 100 | | | | | |

TABLE 2

| O/W emulsions, data in % by weight | | | | | | | | | | |
|---|---|---|---|---|---|---|---|---|---|---|
| | 2-1 | 2-2 | 2-3 | 2-4 | 2-5 | 2-6 | 2-7 | 2-8 | 2-9 | 2-10 |
| Titanium Dioxide | | 2 | 5 | | | | | | | 3 |
| Methylene Bis-benzotriazolyl Tetramethylbutylphenol | | | | | | 1 | 2 | 1 | | |
| 2-(1-Ethylhexyl)-5,7-dihydroxy-chromen-4-one | | | | 1 | 2 | | | | 1 | 1 |
| 4'-Methoxy-6-hydroxyflavone | 1 | 3 | | 2 | | 5 | | 5 | 2 | |
| 2-(Methoxy-methyl)-5,7-dihydroxchromen-4-one | 5 | 5 | 5 | 5 | 5 | 5 | 5 | 5 | 5 | 5 |
| 2-Carboxy-5,7-dihydroxy-chromen-4-one | 1 | 5 | 4 | | 6 | | 7 | | 2 | 1 |
| 4-Methylbenzylidene Camphor | 2 | | 3 | | 4 | | 3 | | 2 | |
| BMDBM | 1 | 3 | | 3 | 3 | | 3 | 3 | 3 | |
| Stearyl Alcohol (and) Steareth-7 (and) Steareth-10 | 3 | 3 | 3 | 3 | 3 | 3 | 3 | 3 | 3 | 3 |
| Glyceryl Stearate (and) Ceteth-20 | 3 | 3 | 3 | 3 | 3 | 3 | 3 | 3 | 3 | 3 |
| Glyceryl Stearate | 3 | 3 | 3 | 3 | 3 | 3 | 3 | 3 | 3 | 3 |
| Microwax | 1 | 1 | 1 | 1 | 1 | 1 | 1 | 1 | 1 | 1 |
| Cetearyl Octanoate | 11.5 | 11.5 | 11.5 | 11.5 | 11.5 | 11.5 | 11.5 | 11.5 | 11.5 | 11.5 |
| Caprylic/Capric Triglyceride | 6 | 6 | 6 | 6 | 6 | 6 | 6 | 6 | 6 | 6 |
| Oleyl Oleate | 6 | 6 | 6 | 6 | 6 | 6 | 6 | 6 | 6 | 6 |
| Propylene Glycol | 4 | 4 | 4 | 4 | 4 | 4 | 4 | 4 | 4 | 4 |
| Glyceryl Stearate SE | | | | | | | | | | |
| Stearic Acid | | | | | | | | | | |
| *Persea Gratissima* | | | | | | | | | | |
| Propylparaben | 0.05 | 0.05 | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 | 0.15 | 0.15 |
| Tromethamine | | | 1.8 | | | | | | | |
| Glycerine | | | | | | | | | | |
| Water | to 100 | to 100 | to 100 | to 100 | to 100 | to 100 | to 100 | to 100 | to 100 | to 100 |

| | 2-11 | 2-12 | 2-13 | 2-14 | 2-15 | 2-16 | 2-17 | 2-18 |
|---|---|---|---|---|---|---|---|---|
| Titanium Dioxide | 3 | | 2 | | | | 2 | 5 |
| Benzylidene Malonate Polysiloxane | | 1 | 0.5 | | | | | |
| Methylene Bis-benzotriazolyl Tetramethylbutylphenol | 1 | 1 | 0.5 | | | | | |
| 4'-Methoxy-7-β-glucoside Flavone | | | | 1 | 2 | | | |
| 2-Carboxyl-5,7-dihydroxychromen-4-one | 1 | 3 | | 2 | | 5 | | 5 |
| 2-Carboxy-7-hydroxychromen-4-one | 5 | 5 | 5 | 5 | 5 | 5 | 5 | 5 |
| Ethyl 5,7-Dihydroxychromen-4-one-2-carboxylate | 1 | 5 | 4 | | 6 | | 7 | |
| Zinc Oxide | | | | 2 | | | | |
| UV-Pearl, OMC | 15 | 15 | 15 | 30 | 30 | 30 | 15 | 15 |
| 4-Methyhlbenzylidene Camphor | | | | 3 | | | | |
| BMDBM | | | | 1 | | | | |
| Phenylbenzimidazole Sulfonic Acid | | | | | 4 | | | |
| Stearyl Alcohol (and) Steareth-7 (and) Steareth-10 | 3 | 3 | 3 | 3 | | | | |
| Glyceryl Stearate (and) Ceteth-20 | 3 | 3 | 3 | 3 | | | | |
| Glyceryl Stearate | 3 | 3 | 3 | 3 | | | | |
| Microwax | 1 | 1 | 1 | 1 | | | | |
| Cetearyl Octanoate | 11.5 | 11.5 | 11.5 | 11.5 | | | | |
| Caprylic/Capric Triglyceride | 6 | 6 | 6 | 6 | 14 | 14 | 14 | 14 |
| Oleyl Oleate | 6 | 6 | 6 | 6 | | | | |
| Propylene Glycol | 4 | 4 | 4 | 4 | | | | |

TABLE 2-continued

| O/W emulsions, data in % by weight | | | | | | | | |
|---|---|---|---|---|---|---|---|---|
| Glyceryl Stearate SE | | | | | 6 | 6 | 6 | 6 |
| Stearic Acid | | | | | 2 | 2 | 2 | 2 |
| *Persea Gratissima* | | | | | 8 | 8 | 8 | 8 |
| Propylparaben | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 |
| Tromethamine | | | | | 1.8 | | | |
| Glycerine | | | | | 3 | 3 | 3 | 3 |
| Water | to 100 | to 100 | to 100 | to 100 | to 100 | to 100 | to 100 | to 100 |

| | 2-19 | 2-20 | 2-21 | 2-22 | 2-23 | 2-24 | 2-25 | 2-26 | 2-27 | 2-28 |
|---|---|---|---|---|---|---|---|---|---|---|
| Titanium Dioxide | | | | | | | 3 | 3 | | 2 |
| Benzylidene Malonate Poylsiloxane | 1 | 2 | | | 1 | 1 | | | 1 | 0.5 |
| 7,8,3'4'-Tetrahydroxyflavone | | | | 1 | 2 | | | | 1 | 1 |
| Ethyl 5,7-Dihydroxychromen-4-on-2-carboxylate | 1 | 3 | | 2 | | 5 | | 5 | 2 | |
| 2-Methyl-5,7-dihydroxy-chromen-4-one | 5 | 5 | 5 | 5 | 5 | 5 | 5 | 5 | 5 | 5 |
| Methylene Bis-benzotriazolyl Tetramethylbutylphenol | | 1 | 2 | 1 | | | | 1 | 1 | 0.5 |
| Zinc Oxide | | | | | 5 | 2 | | | | 2 |
| UV-Pearl, OMC | 15 | 15 | 15 | 15 | 15 | 15 | 15 | 15 | 15 | 15 |
| Caprylic/Capric Triglyceride | 14 | 14 | 14 | 14 | 14 | 14 | 14 | 14 | 14 | 14 |
| Oleyl Oleate | | | | | | | | | | |
| Propylene Glycol | | | | | | | | | | |
| Glyceryl Stearate SE | 6 | 6 | 6 | 6 | 6 | 6 | 6 | 6 | 6 | 6 |
| Stearic Acid | 2 | 2 | 2 | 2 | 2 | 2 | 2 | 2 | 2 | 2 |
| *Persea Gratissima* | 8 | 8 | 8 | 8 | 8 | 8 | 8 | 8 | 8 | 8 |
| Propylparaben | 0.05 | 0.05 | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 | 0.15 | 0.15 |
| Glyceryl Stearate, Ceteareth-20, Ceteareth-10, Cetearyl Alcohol, Cetyl Palmitate | | | | | | | | | | |
| Ceteareth-30 | | | | | | | | | | |
| Dicaprylyl Ether | | | | | | | | | | |
| Hexyldecanol, Hexyldexyl Laurate | | | | | | | | | | |
| Cocoglycerides | | | | | | | | | | |
| Tromethamine | | | | | | | | | | |
| Glycerine | 3 | 3 | 3 | 3 | 3 | 3 | 3 | 3 | 3 | 3 |
| Water | to 100 | to 100 | to 100 | to 100 | to 100 | to 100 | to 100 | to 100 | to 100 | to 100 |

TABLE 3

| Gels, data in % by weight | | | | | | | | | | |
|---|---|---|---|---|---|---|---|---|---|---|
| | 3-1 | 3-2 | 3-3 | 3-4 | 3-5 | 3-6 | 3-7 | 3-8 | 3-9 | 3-10 |
| a = aqueous gel | | | | | | | | | | |
| Titanium Dioxide | | 2 | 5 | | | | | | | 3 |
| 2-Methyl-5,7-Dihydroxychromen-4-one | | | | 1 | 2 | | | | 1 | 1 |
| Ethyl 5,7-Dihydroxy-chromen-4-one-2-carboxylate | 1 | 3 | | 2 | | 5 | | 5 | 2 | |
| Benzylidene Malonate Polysiloxane | | | 1 | 1 | 2 | | | | 1 | 1 |
| Methylene Bis-benzotriazolyl Tetramethylbutylphenol | | 1 | | | | 1 | 2 | 1 | | |
| Zinc Oxide | | | | 2 | | | | 5 | 2 | |
| UV-Pearl, Ethylhexyl Methoxycinnamate | 30 | 15 | 15 | 15 | 15 | 15 | 15 | 15 | 15 | 15 |
| 4-Methylbenzylidene Camphor | | | | | 2 | | | | | |
| Butylmethoxydibenzoylmethane | | 1 | | | | | | | | |
| Phenylbenzimidazole Sulfonic Acid | | | 4 | | | | | | | |
| *Prunus Dulcis* | 5 | 5 | 5 | 5 | 5 | 5 | 5 | 5 | 5 | 5 |
| Tocopheryl Acetate | 0.5 | 0.5 | 0.5 | 0.5 | 0.5 | 0.5 | 0.5 | 0.5 | 0.5 | 0.5 |
| Caprylic/Capric Triglyceride | 3 | 3 | 3 | 3 | 3 | 3 | 3 | 3 | 3 | 3 |
| Octyldodecanol | 2 | 2 | 2 | 2 | 2 | 2 | 2 | 2 | 2 | 2 |

TABLE 3-continued

| | \multicolumn{10}{c}{Gels, data in % by weight} |
|---|---|---|---|---|---|---|---|---|---|---|
| | 3-1 | 3-2 | 3-3 | 3-4 | 3-5 | 3-6 | 3-7 | 3-8 | 3-9 | 3-10 |
| Decyl Oleate | 2 | 2 | 2 | 2 | 2 | 2 | 2 | 2 | 2 | 2 |
| PEG-8 (and) Tocopherol (and) Ascorbyl Palmitate (and) Ascorbic Acid (and) Citric Acid | 0.05 | 0.05 | 0.05 | 0.05 | 0.05 | 0.05 | 0.05 | 0.05 | 0.05 | 0.05 |
| Sorbitol | 4 | 4 | 4 | 4 | 4 | 4 | 4 | 4 | 4 | 4 |
| Polyacrylamide (and) C13-14 Isoparaffin (and) Laureth-7 | 3 | 3 | 3 | 3 | 3 | 3 | 3 | 3 | 3 | 3 |
| Propylparaben | 0.05 | 0.05 | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 | 0.15 | 0.15 |
| Tromethamine | | | 1.8 | | | | | | | |
| Water | to 100 | to 100 | to 100 | to 100 | to 100 | to 100 | to 100 | to 100 | to 100 | to 100 |

The invention claimed is:

1. A method for reducing or suppressing skin unevenness, wrinkles, fine lines, rough skin or large-pored skin, comprising applying to the skin or hair of a human patient at least one compound of formula Ia

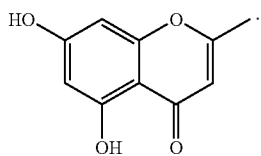

or a salt thereof,
with the proviso that said human is not suffering from pigment defects of the skin.

2. A method according to claim 1, wherein a composition comprising at least one compound of formula Ia or a salt thereof is administered and the composition contains at least one compound of formula II or a salt thereof.

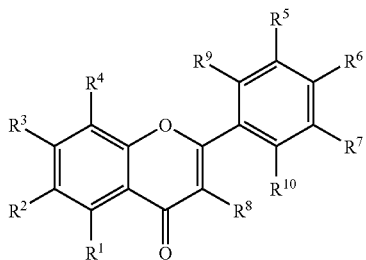

where $R^1$ to $R^{10}$ are identical or different, and are
H
$OR^{11}$
a straight-chain or branched $C_1$- to $C_{20}$-alkyl group,
a straight-chain or branched $C_3$- to $C_{20}$-alkenyl group,
a straight-chain or branched $C_1$- to $C_{20}$-hydroxyalkyl group, where the hydroxyl group is optionally bonded to a primary or secondary carbon atom of the alkyl and wherein the alkyl is optionally interrupted by oxygen,
a $C_3$- to $C_{10}$-cycloalkyl group, or a $C_3$- to $C_{12}$-cycloalkenyl group, where the cyclic group is optionally bridged by —$(CH_2)_n$— group, where n=1 to 3, where all $OR^{11}$ are, independently of one another,
OH
a straight-chain or branched $C_1$- to $C_{20}$-alkoxy group,
a straight-chain or branched $C_3$- to $C_{20}$-alkenyloxy group,
a straight-chain or branched $C_1$- to $C_{20}$-hydroxyalkoxy group, where the hydroxyl group(s) are optionally bonded to a primary or secondary carbon atom of the alkyl and wherein the alkyl is optionally interrupted by oxygen,
a $C_3$- to $C_{10}$-cycloalkoxy group, or $C_3$- to $C_{12}$-cycloalkenyloxy group, where the cyclic group is optionally bridged by —$(CH_2)_n$-group, where n=1 to 3, or
a mono- or oligoglycosyl radical,
with the proviso that at least 4 radicals from $R^1$ to $R^7$ are OH and that the compound of formula II contains at least two pairs of adjacent —OH groups, or $R^2$, $R^5$ and $R^6$ are OH and the radicals $R^1$, $R^3$, $R^4$ and $R^{7-10}$ are H.

3. A method according to claim 1, wherein the method is for reducing skin unevenness, wrinkles, fine lines, rough skin or large-pored skin.

4. A method according to claim 1, wherein the method is for reducing wrinkles.

5. A method according to claim 1, wherein the method is for the suppressing skin unevenness, wrinkles, fine lines, rough skin or large-pored skin.

6. A method according to claim 1, wherein a composition comprising at least one compound of formula Ia or a salt thereof is administered and the composition contains at least one further skin-care ingredient, which is a pyrimidinecarboxylic acid, aryl oxime, or ectoine.

7. A method according to claim 2, wherein the method is for reducing skin unevenness, wrinkles, fine lines, rough skin or large-pored skin.

8. A method according to claim 2, wherein the method is for reducing of wrinkles.

9. A method according to claim 2, wherein the method is for suppressing skin unevenness, wrinkles, fine lines, rough skin or large-pored skin.

10. A method according to claim 2, wherein a composition comprising at least one compound of formula Ia or a salt thereof is administered and the composition contains at least one further skin-care ingredient, which is a pyrimidinecarboxylic acid, aryl oxime, or ectoine.

* * * * *